(12) United States Patent
Hellerstein

(10) Patent No.: US 7,001,587 B2
(45) Date of Patent: Feb. 21, 2006

(54) MEASUREMENT OF PROTEIN SYNTHESIS RATES IN HUMANS AND EXPERIMENTAL SYSTEMS BY USE OF ISOTOPICALLY LABELED WATER

(75) Inventor: Marc K. Hellerstein, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 185 days.

(21) Appl. No.: 10/279,399

(22) Filed: Oct. 23, 2002

(65) Prior Publication Data

US 2003/0133871 A1 Jul. 17, 2003

Related U.S. Application Data

(60) Provisional application No. 60/335,029, filed on Oct. 24, 2001.

(51) Int. Cl.
*A61K 49/00* (2006.01)
*A61K 33/00* (2006.01)
*C12Q 1/00* (2006.01)

(52) U.S. Cl. .............................. 424/9.1; 424/600; 435/4
(58) Field of Classification Search .................... 435/4; 424/9.1, 600
See application file for complete search history.

(56) References Cited

U.S. PATENT DOCUMENTS

| | | | |
|---|---|---|---|
| 4,332,784 A | 6/1982 | Smith et al. | |
| 5,338,686 A | * 8/1994 | Hellerstein | ................. 436/173 |
| 5,439,803 A | 8/1995 | Ross et al. | |
| 5,910,403 A | 6/1999 | Hellerstein | |
| 5,961,470 A | 10/1999 | Wagner et al. | |
| 6,010,846 A | 1/2000 | Hellerstein | |
| 6,461,806 B1 | 10/2002 | Hellerstein | |
| 6,461,870 B1 | 10/2002 | Yatscoff et al. | |
| 6,468,802 B1 | 10/2002 | Yatscoff et al. | |
| 6,599,750 B1 | 7/2003 | Yatscoff et al. | |
| 6,602,715 B1 | 8/2003 | Yatscoff et al. | |
| 6,653,076 B1 | 11/2003 | Franza, Jr. et al. | |
| 6,653,090 B1 | 11/2003 | Lopaschuk | |
| 6,808,875 B1 | 10/2004 | Hellerstein | |
| 2003/0133871 A1 | 7/2003 | Hellerstein | |
| 2003/0148533 A1 | 8/2003 | Malloy et al. | |
| 2003/0180710 A1 | 9/2003 | Lee et al. | |
| 2003/0180800 A1 | 9/2003 | Lee et al. | |
| 2003/0224420 A1 | 12/2003 | Hellerstein | |
| 2003/0228259 A1 | 12/2003 | Hellerstein | |
| 2004/0081994 A1 | 4/2004 | Hellerstein | |
| 2004/0091943 A1 | 5/2004 | Schneider | |
| 2004/0115131 A1 | 6/2004 | Hellerstein | |
| 2004/0152994 A1 | 8/2004 | Meier-Augenstein | |
| 2004/0253647 A1 | 12/2004 | Mathews et al. | |
| 2005/0019251 A1 | 1/2005 | Hellerstein | |
| 2005/0053992 A1 | 3/2005 | Hellerstein | |
| 2005/0147558 A1 | 7/2005 | Hellerstein | |

FOREIGN PATENT DOCUMENTS

| | | |
|---|---|---|
| WO | WO-90/11371 A1 | 10/1990 |
| WO | WO-93/25705 A1 | 12/1993 |
| WO | WO 98/51820 | 11/1998 |
| WO | WO-03/061479 A1 | 7/2003 |
| WO | WO-03/068919 A2 | 8/2003 |
| WO | WO-03/087314 A2 | 10/2003 |
| WO | WO-04/003493 A2 | 1/2004 |
| WO | WO-04/011426 A2 | 2/2004 |
| WO | WO-04/021863 A2 | 3/2004 |
| WO | WO-04/024941 A2 | 3/2004 |
| WO | WO-04/025270 A2 | 3/2004 |
| WO | WO-04/042360 A2 | 5/2004 |
| WO | WO-05/009597 A2 | 2/2005 |
| WO | WO-05/015155 A2 | 2/2005 |
| WO | WO-05/033652 A2 | 4/2005 |

OTHER PUBLICATIONS

Jones et al., "Interaction of Dietary Fat Saturation and Cholesterol Level on Cholesterol Synthesis Measured Using Deuterium Incorporation", Journal of Lipid Research, vol. 35, 1994, pp. 1093-1101.*
Ajie et al., "In Vivo Study of the Biosynthesis of Long Chain Fatty Acids Using Deuterium Water", Am J Physiology, 1995, 269 (2 Pt 1):E247-52.*
U.S. Appl. No. 10/155,536, filed May 24, 2002, Hellerstein.
Airhart, J., A. Vidrich, and E. A. Khairallah. Compartmentation of free amino acids for protein synthesis in rat liver. *Biochem J* 140: 539-45, 1974.
Bonotto, S., I. Ndoite, G. Nuyts, E. Fagniart, and R. Kirchmon. Study of the distribution and biological effects of $^3H$ in the Algae Acetabularia, Chlamydomonas and Porphyra. *Curr Top Rad Quart* 12: 115-132, 1977.
Chinkes, D. L., A. Aarsland, J. Rosenblatt, and R. R. Wolfe. Comparison of mass isotopomer dilution methods used to calculate VLDL production in vivo. *Am. J. Physiol.* 271 (*Endocrinol. Metab.* 34): E373-E383, 1996.
Conrads, Thomas P. and Timothy D. Veenstra. Stable Isotope Labeling in Proteomics *The Synthesis Cambridge Isotope Laboratories* 3 (2): 1-3, Jan. 2002.
Etnier, E., C. Travis, and D. Hetrick. Metabolism of organically bound tritium in man. *Rad Res* 100: 487-502, 1984.
Hellerstein, Marc K. et al. Measurement of synthesis rates of slow-turnover proteins from $^2H_2O$ incorporation into non-essential amino acids (NEAA) and application of mass isotopomer distribution analysis (MIDA). *Faseb Journal Experimental Biology 2002: Meeting Abstracts* 16: pp A256, 2002.

(Continued)

*Primary Examiner*—Leon B. Lankford, Jr.
*Assistant Examiner*—Lora E Barnhart
(74) *Attorney, Agent, or Firm*—Morrison & Foerster LLP

(57) ABSTRACT

Provided herein are methods for measuring protein biosynthesis by using $^2H_2O$ or radioactive $^3H_2O$ and applicable uses thereof.

14 Claims, 18 Drawing Sheets

OTHER PUBLICATIONS

Hellerstein, M. K., and R. A. Neese. Mass isotopomer distribution analysis at eight years: theoretical, analytic, and experimental considerations. *Am J Physiol* 276: E1146-70, 1999.

Hellerstein, M. K., and R. A. Neese. Mass isotopomer distribution analysis: a technique for measuring biosynthesis and turnover of polymers. *Am J Physiol* 263: E988-1001, 1992.

Hellerstein, M. K. Methods for measurement of fatty acid and cholesterol metabolism. *Current Opinion in Lipidology* 6: 172-181, 1995.

Humphrey, T., and D. Davies, A new method for the measurement of protein turnover. *Biochem J* 148: 119-127, 1975.

Humphrey, T., and D. Davies. A sensitive method for measuring protein turnover based on the measurement of 2-$^3$H-labeled amino acids in proteins. *Biochem J* 156: 561-568, 1976.

Jungas, R. L. Fatty acid synthesis in adipose tissue incubated in tritiated water. *Biochemistry* 7: 3708-17, 1968.

Katz, J., and R. Rognstad. Futile cycles in the metabolism of glucose. *Curr Top Cell Regul* 10: 237-89, 1976.

Kelleher, J. K., and T. M. Masterson. Model equations for condensation biosynthesis using stable isotopes and radioisotopes. *Am. J. Physiol.* 262 (*Endocrinol. Metab.* 25): E118-E125, 1992.

Khairallah, E. A., and G. E. Mortimore. Assessment of protein turnover in perfused rat liver. Evidence for amino acid compartmentation from differential labeling of free and tRNA-gound valine. *J Biol Chem* 251: 1375-84, 1976.

Kim, J. et al. "A New Stable Isotope-Mass Spectrometric (MS) Method to Measure Proliferation Rates of Colon Epithelial Cells" *Faseb Journal* 14 (4): pp A718, 2000.

Mathur-De vré, R., and J. Binet. Molecular aspects of tritiated water and natural water in radiation biology, *Prog Biophys Molec Biol* 43: 161-193, 1984.

Mewissen, D., M. Furedi, A. Ugarte, and J. Rust. Comparative incorporation of tritium from tritiated water vs tritiated thymidine, uridine or leucine. *Curr Top Rad Res Quart* 12: 225-254, 1977.

Papageorgopoulos, Christina et al. Measuring Protein Synthesis by Mass Isotopomer Distribution Analysis (MIDA) *Analytical Biochemistry* 267: 1-16, 1999.

Patterson, B. W., and R. R. Wolfe. Concentration dependence of methyl-palmitate isotope ratios by electron impact ionization gas chromatography/mass spectrometry. *Biol. Mass Spectrom.* 22: 481-486, 1993.

Previs, Stephen F. et al. Estimation of Protein Turnover In Vivo Using $D_2O$. *Diabetes Abstract Book, 61st Scientific Sessions*, vol. 50 Supplement 2: A301, Jun. 2001.

van Hinsbergh, V.W.M., et al. Palmitate Oxidation by Rat Skeletal Muscle Mitochondria, *Archives of Biochemistry and Biophysics* 190 (2): 762-771, 1978.

Veerkamp, Jacques H. et al. $^{14}CO_2$ Production Is No Adequate Measure of [$^{14}$C]Fatty Acid Oxidation. *Biochem Medicine and Metabolic Biology* 35: 248-259 (1986).

Bingham, SA (Jan. 1994) "The use of 24-h urine samples and energy expenditure to validate dietary assessments" *American Journal of Clinical Nutrition* 59 (1 suppl): pp. 227S-231S.

Craig, SB et al. (Sep. 1996) "The Impact of Physical Activity on Lipids, Lipoproteins, and Blood Pressure in Preadolescent Girls" *Pediatrics* (3 Pt 1): pp. 389-395.

McCune, Joseph M. et al. "Factors Influencing T-Cell Turnover in HIV-1-Seropositive Patients." *The Journal of Clinical Investigation* 105:R1-R8, Oct. 1999.

Christiansen Mark P. et al. "Effect of Dietary Energy Restriction on Glucose Production and Substrate Utilization in Type 2 Diabetes." *Diabetes* 49: 1691-1699, Oct. 2000.

Wang, Wei et al. "Effects of Nicotinic Acid on Fatty Acid Kinetics, Fuel Selection, and Pathways of Glucose Production in Women." *Am. J. Physiol. Endocrinol. Metab.* 279: E50-E59, 2000.

Parks, Elizabeth J. et al. "Carbohydrate-induced Hypertriacylglycerolemia: Historical Perspective and Review of Biological Mechanisms." *Am. J. Nutr.* 2000; 71:412-433.

Leung, Gordon K. et al. "A Deficiency of Microsomal Triglyceride Transfer Protein Reduces Apolipoprotein B Secretion." *The Journal of Biological Chemistry* 275, No. 11:7515-7520, 2000.

Hudgins, Lisa C. et al. "Relationship Between Carbohydrate-Induced Hypertriglyceridemia and Fatty Synthesis in Lean and Obese Subjects." *Journal of Lipid Research* 41:595-604, 2000.

Davis, Ajuah et al. "Effect of Pinitol Treatment on Insulin Action in Subjects With Insulin Resistance." *Diabetes Care* 23, No. 23:1000-1005, 2000.

Lammert, Ole et al. "Effects of Isoenergetic Overfeeding of Either Carbohydrate or Fat in Young Men." *British Journal of Nutrition* 84:233-245, 2000.

Parks, Elizabeth J. et al. "Dependence ot Plasma α-Tocopherol Flux on Very Low-Density Triglyceride Clearance in Humans." *Free Radical Biology & Medicine* 29, No. 11: 1151-1159, 2000.

Véniant, Murielle M. et al. "Defining the Atherogenicity of Large and Small Lipoproteins Containing Apolipoproteins B100." *The Journal of Clinical Investigation* 106, No. 12: 1501-1510, 2000.

Fagerquist, Clifton K. et al. "Elimination of the Concentration Dependence in Mass Isotopomer Abundance Mass Spectrometry of Methyl Palmitate Using Metastable Atom Bombardment." *J. Am. Soc. Mass Spectrometry* 12:754-761, 2001.

Hellerstein, M. et al. "Directly Measured Kinetics of Circulating T Lymphocytes in Normal and HIV-1-Infected Humans." *Nature Medicine* 5, No. 1:83-89. 1999.

Teixeira, Luciléia et al. "Poor CD4 T Cell Restoration After Supression of HIV-1 Replication May Reflect Lower Thymic Function." *AIDS* 15, No. 14:1749-1756, 2001.

Hellerstein, Marc K. "No Common Energy: de Novo Lipogenesis as the Road Less Traveled." *Am. J. Clin. Nutr.* 74:707-708, 2001.

Neese, Richard A. et al. "Advances in the Stable Isotope-Mass Spectrometric Measurement of DNA Synthesis and Cell Proliferation." *Analytical Biochemistry* Feb. 14, 2001.

Mohri, Hiroshi et al. "Increased Turnover of T Lymphocytes in HIV-1 Infection and its Reduction by Antiretroviral Therapy." *J. Exp. Med.* 194, No. 9: 1277-1287.

Pantaleo, Giuseppe "Unraveling the Strands of HIV's Web." *Nature Medicine* 5, No. 1: 27-28, 1999.

Hellerstein, Marc K. "Carbohydrate-Induced Hypertriglyceridemia: Modifying Factors and Implications for Cardiovascular Risk." *Nutrition and Metabolism.* pp 33-40, 2002.

Trappe, T. A. et al. "Effect of Ibuprofen and Acetaminophen on Postexercise Muscle Protein Synthesis." *Am. J. Physiol. Endocronol Metab* 282:E551-E556, 2002.

Deeks, Steven G. et al. "CD4+ T Cell Kinetics and Activation in Human Immunodeficiency Virus-Infected Patients Who Remain Viremic Despite Long-Term Treatment with Protease Inhibitor-Based Therapy." *The Journal of Infectious Diseases* 185:315-323, 2002.

Neese, R. A. et al. "Measurement of Endogenous Synthesis of Plasma Cholesterol in Rats and Humans Using MIDA." *The American Physiological Society.* pp E139-E147, 1993.

Hellerstein, Marc K. et al. "Model for Measuring Absolute Rates of Hepatic De Novo Lipogenesis and Reesterification of Free Fatty Acids." *The American Physiological Society*: pp E814-E820, 1993.

Hellerstein, Marc K. et al. "Mass Isotopomer Distribution Analysis for Measuring Fluxes Through Intracellular Metabolic Pathways and Biosynthetic Rates of Polymers. *"IFAC Modeling and Control in Biomedical Systems.* pp 353-359, 1994.

Hellerstein, Marc K. et al. "Glycoconjugates as Noninvasive Probes of Intrahepatic Metabolism: Pathways of Glucose Entry into Compartmentalized Hepatic UDP-glucose Pools during Glycogen Accumulation." *Proceedings of the National Academy of Sciences of the United States of America.* 83, Issue 18: 7044-7048, 1986.

Neese, Richard A. et al. "Gluconeogenesis and Intrahepatic Triose Phosphate Flux in Response to Fastinf or Substrate Loads." *The Journal of Biological Chemistry.* 270, No. 24, pp 14452-14463, 1995.

Schwarz, Jean-Marc et al. "Short-Term Alterations in Carbohydrate Energy Intake In Humans." *The American Society for Clinical Investigation.* 96: 2735-2743, 1995.

Hudgins, Lisa C. et al. "Human Fatty Acid Synthesis is Stimulated by a Eucaloric Low Fat, High Carbohydrate Diet." *The American Society for Clinical Investigation.* 97, No. 9: 2081-2091, 1996.

Hellerstein, Marc K. et al. "Measurement of Hepatic $R_a$ UDP-glucose in Vivo in Rats: Relation to Glycogen Deposition and Labeling Patterns." *The American Physiological Society.* pp E155-E162, 1997.

Hellerstein, Marc K. et al. et al. "Altered Fluxes Responsible For Reduced Hepatic Glucose Production and Glusoneogenesis by Exogenous Glucose in Rats." *The American Physiological Society.* pp E162-E172, 1997.

Hellerstein, Marc K. et al. "Hepatic Gluconeogenic Fluxes and Glycogen Turnover During Fasting in Humans." *J. Clin. Invest.* 100, No. 5:1305-1319, 1997.

Dekker, Evelien et al. "Glucose Homeostasis in Children with Falciparum Malaria: Precursor Supply Limits Gluconeogenesis and Glucose Production." *Journal of Clinical Endocrinology and Metabolism.* 82, No. 8: 2514-2519, 1997.

Macallan, Derek C. et al. "Measurement of Cell Proliferation by Labeling of DNA with Stable Isotope-Labeled Glucose: Studies in Vitro, in Animals, and in Humans." *Proc. Natl. Acad. Sci.* 95: 708-713, 1998.

Bandsma. Robert H. J. et al. "Contribution of Newly Synthesized Cholesterol to Rat Plasma and Bile Determined by Mass Isotopomer distribution Analysis: Bile-Salt Flux Promotes Secretion of Newly Synthesized Cholesterol into Bile." *Biochem. J.* 329: 699-703, 1998.

Hoh, Rebecca et al. "De Novo Lipogenesis Predicts Short-Term Body-Composition Response by Bioelectrical Impedance Analysis to Oral Nutritional Supplements in HIV-Associated Wasting." *Am. J. Clin. Nutr.* 68:154-163, 1998.

Siler, Scott Q. et al. "The Inhibition of Gluconeogenesis Following Alcohol in Humans." *The American Physiological Society.* pp E897-E907, 1998.

Siler, Scott Q. et al. "VLDL-Triglyceride Production After Alcohol Ingestion, Studied Using [$2-^{13}C_1$] Glycerol." *Journal of Lipid Research* 39: 2319-2328, 1998.

Van Loan, Marta D. et al. "Monitoring Changes in Fat-Free Mass in HIV-Positive Men With Hypotestosteronemia and AIDS Wasting Syndrome Treated With Gonadal Hormone Replacement Therapy." *AIDS* 13:241-248, 1999.

Fagerquist, Clifton K. et al. "Molecular Ion Fragmentation and Its Effects on Mass Isotopomer Abundance of Fatty Acid Methyl Estes Ionized By Electron Impact." *J. Am. Soc. Mass. Spectrom* 10: 430-439, 1999.

Jung, Hye Rim. et al. "Metabolic Adaptations to Dietary Fat Malabsorption in Chylomicron-Deficient Mice." *Biochem. J.* 343: 473-478, 1999.

Hellerstein, Marc K. et al "The Changing Face of AIDS: Translators Needed." *Am. J. Clin. Nutr.* 70: 787-788, 1999.

Parks, Elizabeth J. et al. "Effects of a Low-Fat, High-Carbohydrate Diet on VLDL-Triglyceride Assembly, Production, and Clearance." *J. Clin. Invest.* 104, No. 8: 1087-1096, 1999.

Wolf, George. "The Effect of Fasting and Fructose and Glucose Infusion on Gluconeogenesis and Triose Phosphate Flux in Rats in Vivo." *Nutrition Reviews.* 53, No., 10: 299-302, 1995.

Hellerstein, Marc K. et al. "Effects of Cigarette Smoking and its Cessation on Lipid Metabolism and Energy Expenditure in Heavy Smokers." *J. Clin. Invest.*93: 265-272, 1994.

Winett, Richard et al. "Exercise Regimens for Men With HIV." *Letters.* pp 175-181 & 2999.

Bandsma. Robert H. J. et al. The Contribution of Newly Synthesized Cholesterol to Bile Salt Synthesis in Rats Quantified By Mass Isotopomer Distribution Analysis. *Biochimica et Biophysica Acta* 1483: 343-351, 2000.

Hellerstein, Marc K. et al. "Measurement of T-Cell Kinetics: Recent Methodologic Advances." *Trends Immunology Today.* 20, No. 10: 438-441, 1999.

Hellerstein, Marc K. et al. "Directly Measured Kinetics of Circulating T Lymphocytes in Normal and HIV-1-Infected Humans." *Nature Medicine*, 5, No. 1: 83-89, 1999.

Misell, L. et al. "A new in vivo Stable Isotope Method for Measuring Mammary Epithelial Cell Proliferation." *Faseb Journal Experimental Biology* 2000 14(4): *Meeting Abstract* 550.5: pp A786.

Scott M. Turner et al. "Measurement of Triglyceride (TG) Synthesis in vivo $^2H_2O$ Incorporation into TG-Glycerol and Application of Mass Isotopomer Distribution Analysis (MIDA)." *Experimental Biology* 2002, 16: *Meeting Abstract* 361.9: pp A400.

Fernando Antelo et al. "Adipose Triglyceride (TG) Turnover and de novo Lipogenesis (DNL) in Humans: Measurement by Long-Term $^2H_2O$ Labeling and Mass Isotopomer Distribution Analysis (MIDA)." *Experimental Biology* 2002, 16: *Meeting Abstract* 361.10: pp A400.

J.C. Waterlow "Protein Turnover in the Whole Animal." *Invest. Cell Pathol.*, 3: 107-119 (1980).

Eugene D. Robin and Ronald Wong. "Mitochondria DNA Molecules and Virtual Number of Mitochondria per Cell in Mammalian Cells." *Journal of Cellular Physiology* 136: 507-513 (1988).

Steven N. Blair, et al. "Changes in Physical Fitness and All-Cause Mortality: A Prospective Study of Healthy and Unhealthy Men." *JAMA*, 273, No. 14: 1093-1098, (1995).

Chong Do Lee, et al. "Cardiorespiratory Fitness, Body Composition, and All-Cause and Cardiovascular Disease Mortality in Men [1-3]." *Am J Clin Nutr*, 69:373-380, (1999).

Giuseppe Attardi and Gottfried Schatz, "Biogenesis of Mitochondria." *Ann. Rev. Cell Biol.* 4:289-333, (1988).

David A. Clayton. "Replication and Transcription of Vertebrate Mitochondrial DNA." *Annu. Rev. Cell Biol.* 7: 453-478, (1991).

Bertani, Roberta et al. "Measurement of Total Body Water (TBW) Through In Vivo Dilution of Tracer Compounds: Use of $D_2O$ and its Determination by FT Infrared Spectroscopy." *Annali diChimica* 92:135-138, Jan. 2002.

Jennings, Graham et al. "The Use of Infrared Spectrophotometry for Measuring Body Water Spaces." *Clinical Chemistry* 45, No. 7: 1077-1081, Jul. 1999.

Roberts, S. B. "Use of the doubly labeled water method for Measurement of Energy Expenditure, Total Body Water, Water Intake, and Metabolizable energyIntake in Humans and Small Animals." *Canadian J of Physiology and Pharmacology*, vol. 67, No. 10: 1190-1198, Oct. 1989.

International Search Report mailed on Apr. 13, 2004, for PCT application no. PCT/US03/20052 filed on Jun. 25, 2003, 3 pages.

Hellerstein, Marc K. "In Vivo Measurement of Fluxes Through Metabolic Pathways: The Missing Link in Functional Genomics and Pharmaceutical Research" *Annu. Rev. Nutr.* 23: 379-402, Mar. 2003.

International Search Report for PCT application PCT/US03/23340, filed Jul. 25, 2003, mailed Aug. 18, 2004: 4 pages.

International Search Report for PCT application PCT/US03/29526, filed Sep. 16, 2003, mailed Aug. 18, 2004: 3 pages.

International Search Report for PCT application PCT/US03/35107, filed Nov. 4, 2003, mailed Jul. 9, 2004: 2 pages.

International Search Report mailed Jul. 8, 2004, for PCT patent application No. PCT/US03/27623 filed on Sep. 4, 2003, 4 pages.

International Search Report mailed on Aug. 20, 2004, for PCT application No. PCT/US03/10554 filed on Apr. 4, 2003, 4 pages.

International Search Report mailed on Jan. 19, 2005, for PCT application No. PCT/US03/29361 filed on Sep. 15, 2003, 4 pages.

International Search Report mailed on Mar. 25, 2005, for PCT application No. PCT/US04/39722 filed on Nov. 24, 2004, 3 pages.

International Search Report mailed on Apr. 4, 2005, for PCT application No. PCT/US04/21063 filed on Jun. 29, 2004, 2 pages.

"New Diagnostic Technique Could Help Treat AIDS," Agence France-Presse, Dow Jones News/Retrieval, Feb. 17, 1998, pp. 1-2.

Adami, H.O. et al. (1995) "The Aetiology and Pathogenesis of Human Breast Cancer" *Mutation Research* 333: 29-35.

Anderson, R.W. et al. (1998) "Direct HIV Cytopathicity Cannot Account for CD4 Decline in AIDS in the Presence of Homeostasis: A Worst-Case Dynamic Analysis" *J. AIDS and Human Retrovirology* 17:245-252.

Asher, E. et al. (1995) "Evaluation of Cell Death in EBV-Transformed Lymphocytes Using Agarose Gel Electrophoresis, Light Microscopy and Electron Microscopy" *Leukemia and Lymphoma* 19:107-119.

Bach, Simon P. et al. (2000) "Stem Cells: The Intestinal Stem as a Paradigm" *Carcinogenesis* 21(3): 469-476.

Bickenbach, J.R. (1981) "Identification and Behavior of Label-Retaining Cells in Oral Mucosa and Skin" *J Dent Res* 1611-1620.

Bier, D.M. (1997) "Stable Isotopes in Biosciences, Their Measurement and Models for Amino Acid Metabolism" *Eur J Pediatr* 156 [*Supp.* 1]: S2-S8.

Black, G.E. et al. (Jan. 2001) "Labeling DNA with Stable Isotopes: Economical and Practical Considerations," *BioTechniques* 30:134-140.

Blau, K. and Halket, J. eds. (1993) *Handbook of Derivatives for Chromatography, 2nd Edition*, John Wiley & Sons Ltd., England.

Bravo, Elena et al. (1994) "Decreased Hepatic Uptake and Processing of High Density Lipoprotein Unesterified Cholesterol and Cholesteryl Ester with Age in the Rat" *J. Biochem.* 116: 1088-1095.

Brown, Alan S. et al (1998) "Treating Patients with Documented Atherosclerosis to National Cholesterol Education Program-Recommended Low-Density-Lipoprotein Cholesterol Goals with Atorvastatin, Fluvastatin, Lovastatin and Simvastatin" *J. Am. Coll. Cardiol.* 32: 665-672.

Bucy, R.P. et al. (1998) "Analysis of Lymph Node Biopsies in HIV Infected Patients Before and After HAART" *Abstract, 5th Conference on Retroviruses and Oppurtunistic Infections, Session 66* 519: 177.

Caldwell, K.A. et al. (1993) "Quantification of Peptide Isotopomer Abundances and Determination of Protein (sic) Turnover Rates by Using Mass Isotopomer Distribution Analysis" *Abstract, 41st Annual Amer. Society Mass Spectrometry on Mass Spectrometry*, p. 331a.

Cassella, C.R. et al. (1997) "Mechanisms of Lymphocyte Killing by HIV" *Current Opinion in Hematology* 4:24-31.

Cesar, D. et al. (1998) "Direct Measurement of CD4+ and CD8+ T Cell Proliferation Rates in Vivo in AIDS Patients Using a Stable Isotope-Mass Spectrometric Technique" *Abstract, 5th Conference on Retroviruses and Opportunistic Infections*, Chicago Illinois.

Cohen, A. et al. (1983) "Purine and Pyrimidine Metabolism in Human T Lymphocytes," *J. Biol. Chem.* 258(20):12334-12340.

Cohen, J. (1998) "Failure Isn't What It Used to Be . . . But Neither is Success" *Science* 279:1133-1134.

Conners, M. et al. (1997) "HIV Infection Induces Changes in CD4+ T-Cell Phenotype and Depletions Within the CD4+ T-Cell Repertoire that are not Immediately Restored by Antiviral or Immune-Based Therapies" *Nature Medicine* 3(5):533-540.

Crain, P.F.(1990) "Preparatin and Enzymatic Hydrolysis of DNA and RNA for Mass Spectrometry," *Meth. Enz.* 193: 782-790.

Deeks, S. et al. (1998) "Viral Load and CD4+ T Cell Changes in Patients Failing Potent Protease Inhibitor Therapy" *Abstract, 5th Conference on Retroviruses and Opportunistic Infections, Session* 53, 419:158.

Dimitrov, D.S. et al. (1995) Scientific Correspondence, *Nature* 375:194-195.

Gorochov, G. et al. (1998) "Perturbation of CD4+ and CD8+ T-Cell Repertoires During Progression to AIDS and Regulation of the CD4+ Repertoire During Antiviral Therapy," *Nature Medicine* 4(2):215-221.

Goz, Barry (1978) "The Effects of Incorporation of 5-Halogenated Deozyuridines into DNA of Eukaryotic Cells" *Macological Reviews* 29(4): 249-272.

Gratzner, H.G. (1982) "Monoclonal Antibody to 5-Broma- and 5-Iododeoxyuridine: A New Reagent for Detection of DNA Replication" *Science* 218:474-475.

Gygi, Steven and Ruedi Aebersold (2000) "Using mass spectrometry for quantitative proteomics" *Proteomics: A Trends Guide*: 31-36.

Hansen, Andrew P. et al. (1992) "A Practical Method for Uniform Isotopic Labeling of Recombinant Proteins in Mammalian Cells" 31 (51): 12713-12718.

Hellerstein, M.K. et al. (1997) "T Cell Turnover in HIV-1 Disease," *Immunity* 7:583-589 (Nov. 1997).

Ho, O.D. et al. (1995) "Rapid Turnover of Plasma Virions and CD4 Lymphocytes in HIV-1 Infection," *Nature* 373: 123-126.

Hsieh, Elaine A. et al. (2004) "Dynamics of Keratinocytes in Vivo Using 2H2O Labeling: A Sensitive Marker of Epidermal Proliferation State," *J Invest Dermatol*, 123: 530-536.

James, J.S. (1998) "Clinical Implications of Virological Failure: Interview with Steven Deeks, M.D., San Francisco General Hospital," *AIDS Treatment News*, 289:6-7.

Lewanczuk, Richard Z. et al. (2004) "Comparison of the [13 C] Glucose Breath Test to the Hyperinsulinemic-Euglycemic Clamp When Determining insulin Resistance" *Diabetes Care* 27(2): 441-447.

Lipkin, M. (1987) "Proliferation and Diffentiation of Normal and Diseased Gastrointestinal Cells" In *Physiology of the Gastrointestinal Tract*, L.R. Johnson ed., Raven Press, New York, pp. 255-284.

Lipkin, Martin et al. (1963) "Cell Proliferation Kinetics in the Gastrointestinal Tract of Man. I. Cell Renewal in Colon and Rectum" *Journal of Clinical Investigations* 42(6): 767-776.

Maentausta, O. et al. (1979) "Radioimmunoassay of Conjugated Cholic Acid, Chenodeoxycholic Acid, and Deoxycholic Acid from Human Serum, with Use of 125I-Labeled Ligands" *Clin. Chem.* 25(2): 264-268.

Margolick, J.B. et al. (1995) "Failure of T-cell Homeostasis Preceding AIDS in HIV-1 Infection," *Nature Medicine*, 1(7):674-680.

McCloskey, J.A. (1990) "Electronlonization Mass Spectra of Trimethylsilyl Derivatives of Nucleosides," *Meth. Enz.* 193:825-841.

McCune, J.M. (1997) "Thymic Function in HIV-1 Disease," *Seminars in Immunology* 9:397-404.

McLean, A.R. et al. (1995) "In Vivo Estimates of Division and Death Rates of Human T Lymphocytes," *Proc. Natl. Acad. Sci USA* 92:3707-3711.

Meier, P.R. et al. (Mar. 1981) "Rates of Protein Synthesis and Turnover in Fetal Life," *Am J Physiol.*, 240(3):E320-E324.

Mellors, J.W. et al. (1995) "Quantitation of HIV-1 RNA in Plasma Predicts Outcome after Seroconversion," *Ann. Intern. Med.* 122:573-579.

Mellors, J.W. et al. (1996) "Prognosis in HIV-1 Infection Predicted by the Quantity of Virus in Plasma," *Science*, 272:1167-70.

Messmer, Bradley T. et al. (Feb. 10, 2005) "In Vivo Measurements Document the Dynamic Cellular Kinetics of Chronic Lymphocytic Leukemia B Cells," *J. Clin. Invest.* doi:10.1172/JCI200523409.

Michie, C.A. et al. (1992) "Lifespan of Human Lymphocyte Subsets Defined by CD45 isoforms," *Nature* 360:264-265.

Morris, Rebecca J. et al. (1986) "Evidence that a Slowly Cycling Subpopulation of Adult Murine Epidermal Cells Retains Carcinogen" *Cancer Research* 46: 3061-3066.

Morris, Rebecca J. et al. (1997) "Evidence that Cutaneous Carcinogen-intitiated Epithelial Cells from Mice are Quiescent Rather that Actively Cycling" *Cancer Research* 57: 3436-3443.

Mosier, D.E. (1995) "$CD4^+$ Cell Turnover," *Nature* 375: 193-194.

Murali-Krishna, K. et al. (1998) "Counting Antigen-Specific CD8 T Cells: A Reevaluation of Bystander Activation during Viral Infection," *Immunity* 8:177-187.

Neese, R. A. et al. (Nov. 2002) "Measurement in vivo of Proliferation Rates of Slow Turnover Cells by 2H2O Labeling of the Deoxyribose Moiety of DNA," *PNAS*, 99(24): 15345-15350.

Ong, Shao-En et al. (2002) "Stable Isotope Labeling by Amino Acids in Cell Culture, SILAC, as a Simple and Accurate Approach to Expression Proteomics" *Molecular and Cellular Proteomics* 1: 376-386.

Oyaizu, N. et al. (1995) "Role of Apoptosis in HIV Disease Pathogenesis," *J. of Clinical Immunology* 15(5):217-231.

Palmer, L.D. et al. (1997) "Telomere Length, Telomerase Activity, and Replicative Potential in HIV Infection: Analysis of CD4+ and CD8+ T Cells from HIV-discordant Monozygotic Twins," *J. Experimental Medicine* 185(7): 1381-1386.

Papageorgopoulos, C. et al.(1993) "Toward the Measurement of Protein Synthesis by Mass Isotopomer Distribution Analysis (MIDA):Resolution of Electrospray/Quadrupole Mass Spectrometry (ESI/MS)," *Abstract, Federation of American Societies for Experimental Biology* 1022:A177.

Park, S. S., et al. (1997) "Measurement of Small Intestinal Cell Turnover with [6,6,2H2] Glucose," *Berkeley Scientific, Abstract* 1(2):41-43.

Paša-Tolić, Ljiljana et al. (1999) "High Throughput Proteome-Wide Precision Measurements of Protein expression Using Mass Spectrometry" *J. Am. Chem. Soc.* 121: 7949-7950.

Patton, G.M. et al. (Jul. 1979) "Measurements of Fatty Acid Synthesis by Incorporation of Deuterium from Deuterated Water," *Biochemistry*, 18(14):3186-3188.

Perelson, A.S. et al.(1996) "HIV-1 Dynamics in Vivo: Virion Clearance Rate, Infected Cell Life-Span, and Viral Generation Time," *Science* 271:1582-1586.

Perelson, A.S. et al.(1997) "Decay Characteristics of HIV-1-Infected Compartments During Combination Therapy," *Nature* 387:188-191.

Pozharisski, K.M. et al. (1980) "Study of Kinetics of Epithelial Cell Populations in Normal tissues of the Rat's Intestines and in Carcinogenesis" *Exp. Path., Bd.* 18:387-406.

Reichard, P. (1978) "From Deoxynucleotides to DNA Synthesis," *Federation Proceedings* 37(1):9-14.

Reichard, P. (1988) "Interactions Between Deoxyribonucleotide and DNA Synthesis," *Ann. Rev. Biochem.* 57:349-374.

Rocha, Benedita et al. (1990) "Accumulation of Bromodeoxyuridine-Lavelled Cells in Central and Peripheral Lymphoid Organs: Minimal Estimates of Production and Turnover Rates of Mature Lymphocytes" *J. Immunol.* 20: 1697-1708.

Roda, Aldo et al. (1980) "Results with Six 'Kit' Radioimmunoassays for Primary Bile Acids in Human Serum Intercompared" *Clin. Chem.* 26(12): 1677-1682.

Roederer, M. (Jul. 1995) "T-Dell Dynamics of Immunodeficiency," *Nature Medicine* 1(7):621-622.

Sawada, S. et al. (1995) "Comparison of Autoradiography, Liquid Scintillation Counting and Immunoenzymatic Staining of 5-bromo-2'-deoxyuridine for Measurement of Unscheduled DNA Synthesis and Replicative DNA Synthesis in Rat Liver," *Mutation Research* 344:109-116.

Scalise, K. (Feb. 11-17, 1998) "Tracking T-Cells in AIDS Patients: A Safe Reliable Method of Measuring Human Cell Generation Rates," *Berkeleyan*, p. 3.

Shevchenko, Andrej et al. (1997) "Rapid 'de Novo' Peptide Sequencing by a Combination of Nanoelectrospray, Isotopic Labeling and a Quadrupole/Time-of-flight Mass Spectrometer" *Rapid Communications in Mass Spectrometry* 11: 1015-1024.

Shigenaga, M.K. et al. (1994) "Assays of Oxidative DNA Damage Biomarkers 8-Oxo-2'-deoxyguanosine and 8-Oxoguanine in Nuclear DNA and Biological Fluids by High-Performance Liquid Chromatography with Electrochemical Detection," *Methods in Enzymology* 234: 16-33.

Smith, et al. (1983) "The Phosphogluconate Oxidative Pathway," in *Principles of Biochemistry, 7th edition*, McGraw-Hill Book Company, pp. 417-423.

Sprent, J. et al. (1995) "CD4+ Cell Turnover," *Nature* 375:194.

Sunter, J.P. et al. (1978) "Cell Population Kinetics in the Epithelium of the Colon of the Male Rat" *Birchows Archiv. B Cell Path*. 26: 275-287.

Tint, G.S. et al. (1974) "Transformation of 5α-cholest-7-en-3β-ol to Cholesterol and Cholestanol in Cerebrotendinous Xanthomatosis" Journal of Lipid Research 15: 256-262.

Traber, P.G. et al. (1991) "Isolation of Intestinal Epithelial Cells for the Study of Differential Gene Expression Along the Crypt-Villus Axis," *Am. J. Physiol.* 260:G895-G903.

Veenstra, Timothy D. et al. (2000) "Proteome Analysis Using Selective Incorporation of Isotopically Labeled Amino Acids" *J. Am. Soc. Mass. Spectrom.* 11:78-82.

Wadke, M. et al. (Jul. 1973) "Fatty Acid Synthesis by Liver Perfused with Deuterated and Tritiated Water," *Biochemistry.*, 12(14):2619-2624.

Wain-Hobson, S. (1995) "Virological Mayhem," *Nature* 373:102.

Waldeman, F.M. et al. (1991) "A Comparison Between Bromodeoxyuridine and 3 H Thymidine Labeling in Human Breast Tumors," *Modern Path.* 4(6):718-722.

Wei, X et al. (1995) "Viral Dynamics in Human Immunodeficiency Virus Type 1 Infection," *Nature* 373:117-122.

Wolfe, R. (1990) "Isotopic Measurement of Glucose and Lactate Kinetics," *Ann. Med.* 22:163-170.

Wolthers et al. (1998) "Rapid CD4+ T-Cell Turnover in HIV-1 Infection: a Paradigm Revisited," *Immunol. Today* 19(1):44-48.

Wolthers, K.C. et al. (1998) "T Cell Telomere Length in HIV-1 Infection: No Evidence for Increased CD4+ T Cell Turnover," *Science* 274:1543-1547.

Wood, H.G. et al. (1963) "Estimation of Pathways of Carbohydrate Metabolism," *Biochemische Zeitschrift* 338: 809-847.

Zhang, Z-Q. et al. (Feb. 1998) "Kinetics of CD4+ T Cell Repopulation of Lymphoid Tissues after Treatment of HIV-1 Infection," *Proc. Natl. Acad. Sci. USA* 95:1154-1159.

Zilversmit, D.B. et al. (1943) "On the Calculation of 'Turnover Time' and 'Turnover Rate' from Experiments Involving the Use of Labeling Agents," *J. of General Physiology* 26(3):325-331.

* cited by examiner

US 7,001,587 B2

MEASUREMENT OF PROTEIN SYNTHESIS RATES IN HUMANS AND EXPERIMENTAL SYSTEMS BY USE OF ISOTOPICALLY LABELED WATER

CROSS-REFERENCE TO RELATED APPLICATIONS

This application claims priority to U.S. patent application Ser. No. 60/335,029 filed on Oct. 24, 2001 which is hereby incorporated by reference in its entirety.

STATEMENT REGARDING FEDERALLY SPONSORED RESEARCH AND DEVELOPMENT

This invention was funded in part by grant number AI44767 and AI41401 from the National Institutes of Health. The U.S. Government may have certain rights to this invention.

FIELD OF THE INVENTION

The field of this invention in biochemical kinetics. More specifically, it relates to the measurement of protein synthesis rates.

BACKGROUND OF THE INVENTION

Publications referred to by reference numbering in this specification correspond to the reference list at the end of the specification are hereby incorporated by reference in their entirety.

Control over protein synthesis rates is involved in the regulation of most biological processes and is believed to be the primary cause of numerous diseases. Regulation of the synthesis rates of biomolecules in living systems is one of the most fundamental features of biochemical and physiologic control. For this reason, measurement of biosynthetic rates in vivo has been the subject of enormous research effort over the past 50 years. Among the macromolecules that have been studied, proteins have received perhaps the most intense attention due to their central role in controlling biological processes. The measurement of protein synthesis, as for all other biomolecules, has traditionally required the use of isotopic labels (stable isotopes or radioisotopes). Many studies have described isotopic studies of protein biosynthesis (see Waterlow, 1978, and Hellerstein & Neese, 1999).

In essence, four general approaches have been described for measuring protein biosynthetic rates (Waterlow, 1979). These are: (1) exogenous labeling of proteins of interest, with subsequent re-introduction into the biological system followed by measurement of die-away curves of the labeled protein; (2) endogenous pulse-labeling of proteins from a labeled biosynthetic precursor, followed by measurement of die-away curves of the labeled proteins of interest; (3) endogenous pulse-labeling of proteins from a labeled biosynthetic precursor, followed by measurement of label incorporation curves into the proteins of interest, and comparison to estimates of the changing content of label present over time in the biosynthetic precursor pool; (4) endogenous labeling of proteins by continuous administration of a labeled biosynthetic precursor, with measurement of label incorporation into the proteins of interest, and comparison to steady-state label content in the biosynthetic precursor pool (use of precursor-product relationship).

Among these general labeling strategies, perhaps the most reliable technically and operationally is the continuous administration of a labeled biosynthetic precursor (approach #4). This approach takes advantage of a mathematical principle known as the precursor-product relationship or, in physics, Newton's cooling equation.

The conceptual basis of the precursor-product relationship is shown in FIG. 1. The central principle is that the label content of the product approaches a known value, or asymptote, which in turn is determined by and measurable as the label content in the biosynthetic precursor pool.

As summarized by Waterlow et al (1979), this use of the precursor-product relationship presents several key practical advantages compared to alternative strategies, particularly when the half-lives of the product pool molecules (e.g., proteins) are longer than the half-lives of the precursor pool molecules (e.g., free amino acids). The first advantage is that if the isotopic enrichment of the amino acid biosynthetic precursor pool can be determined and is relatively stable during the continuous label administration period, only a single time point of the protein end-product is, in principle, required to characterize the synthesis rate of the protein molecule. This is so because the basic precursor-product equation can be used in its integrated form when the precursor pool enrichment ($S_A$) is held steady:

$$dS_B/dt = k(S_A - S_B).$$

If $S_A$ is constant, $S_{B(t)} = S_A(1 - e^{-kt})$ $$S_{B(t)} = k\left[\int_0^t S_A dt - \int_0^t S_B(dt)\right]$$

This relationship is depicted graphically in FIG. 1.

Accordingly, multiple sampling of the protein is not required (unlike decay curves after endogenous or exogenous labeling) and multiple sampling of the precursor pool is not required (unlike pulse-labeling approaches). By maintaining a constant or near-constant isotope enrichment in the precursor pool, problems related to non-steady state corrections, non-homogeneity or incomplete mixing in the amino acid precursor pool are also avoided.

Waterlow et al (1979) showed mathematically that synthesis rates are rigorously calculable by this approach even when the protein mass is increasing or decreasing (i.e., if there is a non-steady state in the end-product pool). This feature allows for broad application of this approach, regardless of the physiologic conditions present in the system being studied.

There are some practical disadvantages of the continuous administration approach, however. The most important of these are: (1) the need for continuous administration of the isotopically labeled biosynthetic precursor, in order to maintain relative steady isotopic enrichments in the precursor amino acid pool. This requirement typically necessitates continuous intravenous infusion or frequent repeated oral dosing over many days, or even longer. The need for intravenous administration severely constrains routine medical diagnostic or field use of this approach; (2) the potentially high cost of maintaining a constant level of label in the biosynthetic precursor pool for a relatively long period of time; (3) the need to measure the interim isotopic enrichment of the biosynthetic precursor pool and establish its constancy; and (4) problems in identifying the "true precursor" pool for protein biosynthesis in living cells and individuals.

The problem of identifying the true precursor pool for biosynthesis applies to all applications of the precursor-product relationship, not just for protein synthesis, and derives from the central principle of the technique: the assumption that the labeling curve in the product approaches a known asymptote, or plateau value, which is determined by the label content of the precursor pool (FIG. 1). It is therefore essential to establish during any labeling study the actual asymptotic or plateau value that is being approached. This asymptote value can either be established by waiting long enough to allow the complete shape of the labeling curve in the product molecule to become apparent (FIG. 1) or by using a surrogate measure based upon the known biochemical organization of the protein biosynthetic system (i.e., from the label content in the free amino acid pool leading to protein synthesis). However, the biochemical organization of protein synthesis is extremely complex and unpredictable, making the latter approach subject to significant systematic errors (Waterlow 1979; Airhart 1974; Khairallah and Mortimore 1976).

Alternatively, allowing the shape of the curve to become apparent requires continuous administration for several half-lives of the protein end-product. This requirement is most often not practical, in that protein half-lives may be several days, weeks or months. It is not practical to maintain an intravenous infusion for more than 24 to 48 hours (even intravenous infusions of this length require medical personnel and monitoring) and oral administration of precursor metabolites cannot achieve stable values in metabolic pools.

Accordingly, it has long been recognized in the field (Waterlow 1979; Hellerstein and Neese 1992; Hellerstein and Neese 1999) that an ideal method would allow constant isotope levels in the precursor pool to be maintained for prolonged periods of time in a simple, non-demanding manner, for example, on the order of a few half-lives of long-lived proteins. However, there has not been a technique that has fulfilled this objective. A method for measuring protein synthesis that is widely applicable, reliable, easy to perform, inexpensive, without toxicities or complications, applicable in human subjects, free of the need for medical supervision or in-patient procedures (such as intravenous infusions), does not require complex instructions, and possesses the advantages of simple interpretation, therefore would be extremely valuable and useful in fields ranging from medical diagnostics to drug discovery, genetics, functional genomics, and basic research.

BRIEF SUMMARY OF THE INVENTION

In order to meet these needs, the present invention is directed to methods of determining the biosynthetic or degradation rate of one or more proteins or peptides, methods of using the biosynthetic rate and/or degradation rate determination methods in diagnosis and testing, and kits for determining protein or peptide biosynthetic rates and/or degradation rates.

In one variation, the invention includes a method of determining the biosynthetic rate of one or more proteins or peptides in an individual by: (a) administering $^2$H, $^3$H, and $^{18}$O labeled water to an individual over a period of time sufficient for the label of the labeled water to be incorporated into one or more proteins or peptides to form labeled and unlabeled proteins or peptides; (b) obtaining one or more bodily tissues or fluids from the individual, where bodily tissues or fluids include the one or more labeled and unlabeled proteins or peptides; and (c) detecting the incorporation of the label in the one or more labeled proteins or peptides to determine the biosynthetic rate of the one or more proteins or peptides.

In another variation, the invention includes a continuous labeling method of determining the biosynthetic rate of one or more proteins or peptides in an individual by: (a) administering water labeled with $^2$H, $^3$H, or $^{18}$O to an individual over a period of time sufficient to maintain relatively constant water enrichments; (b) obtaining one or more bodily tissues or fluids from the individual, wherein the bodily tissues or fluids comprise the one or more proteins or peptides; (c) measuring incorporation of the label into the one or more proteins or peptides; (d) calculating the isotopic enrichment values of the one or more proteins or peptides; and (e) applying a precursor-product relationship to the isotopic enrichment values in order to determine the biosynthetic rate of the one or more proteins or peptides.

In another variation, the isotope enrichment values of the proteins or peptides may be compared to either to water enrichment values in the individual or to the isotopic plateau value approached by labeled amino acids.

In another variation, the invention includes a method of determining the biosynthetic rate of one or more proteins or peptides in an individual by (a) administering $^2$H, $^3$H, and/or $^{18}$O labeled water to an individual over a period of time sufficient for the label to be incorporated into the one or more proteins or peptides and thereby form labeled and unlabeled proteins or peptides; (b) obtaining one or more bodily tissues or fluids from the individual; (c) hydrolyzing one or more labeled and unlabeled proteins in the one or more bodily tissues or fluids to produce one or more labeled and unlabeled amino acids; and (d) detecting the incorporation of the label in the one or more labeled amino acids to determine the biosynthetic rate of the one or more proteins or peptides.

The present invention is further directed to a method of determining the degradation rate of one or more proteins or peptides in an individual comprising the steps of (a) administering $^2$H, $^3$H, and/or $^{18}$O labeled water to an individual over a period of time sufficient for the label to be incorporated into one or more proteins or peptides to form labeled and unlabeled proteins or peptides; (b) discontinuing the administering step (a); (c) obtaining one or more bodily tissues or fluids from the individual, wherein the bodily tissues or fluids include one or more labeled and unlabeled proteins or peptides; and (d) detecting the incorporation of the label in the one or more labeled amino acids to determine the degradation rate of the one or more proteins or peptides.

In another variation, the invention involves a discontinuous labeling method for determining the degradation rate of one or more proteins or peptides in an individual by: (a) administering water labeled with $^2$H, $^3$H, and $^{18}$O to an individual; (b) discontinuing administering the labeled water; (c) obtaining one or more bodily tissues or fluids from the individual, wherein the bodily tissues or fluids include one or more proteins or peptides; (d) measuring incorporation of the label into the proteins or peptides; (e) calculating the isotopic enrichment values of the one or more proteins or peptides; and (f) applying an exponential decay relationship to the isotopic enrichment values to determine the degradation rate of the one or more proteins or peptides.

In another variation of both continuous and discontinuous labeling methods, the label is $^2$H.

In another variation, both continuous and discontinuous labeling methods may optionally include partially purifying one or more proteins or peptides from the bodily tissues or fluids before the measuring step. The partial purification may further include isolating one of the one or more proteins or peptides.

In another variation, the methods may comprise detecting the one or more proteins or peptides by mass spectrometry or liquid scintillation counting. The methods may also optionally be accomplished by mass spectrometry alone. In a further variation, the methods may be accomplished by liquid scintillation counting alone.

In a further variation, the labeled water of both methods may optionally be administered orally.

In another variation, the measured proteins or peptides include, but are not limited to, full length proteins or peptide fragments of bone collagen, liver collagen, lung collagen, cardiac collagen, muscle myosin, serum hormone, plasma apolipoproteins, serum albumin, clotting factor, immunoglobulin, and mitochondrial protein.

In a further variation, both methods may further include hydrolyzing the one or more proteins or peptides to produce amino acids, and/or optionally, oligoproteins, prior to measuring isotope incorporation. The amino acids or oligopeptides may optionally be separated by gas chromatography or HPLC. The gas chromatograph or HPLC may or may not be coupled to the mass spectrometer.

In another variation, the individual of any of the methods is human.

In additional variations, the methods of measuring biosynthetic rates or degradation rates may be used to diagnose, prognose, or monitor diseases, disorders, and treatment regimens. In one variation, the risk of osteoporosis may be identified by determining the biosynthetic or degradation rate of bone collagen. In another variation, a response to hormone replacement therapy may be identified by determining the biosynthetic or degradation rate of bone collagen. In another variation, a response to treatment with a hypolipidemic agent may be identified by determining the biosynthetic or degradation rate of apolipoprotein B. In a further variation, a response to an exercise training or medical rehabilitation regimen may be identified by determining the biosynthetic or degradation rate of one or more muscle proteins. In yet a further variation, a index of hypertrophy versus hyperplasia by measuring the ratio of protein: DNA synthesis rates in a tissue may be determined by determining the biosynthetic rate or degradation rate. In a further variation, the presence or titer of a specific immunoglobulin in an individual after vaccination or after an infectious exposure may be identified by determining the biosynthetic rate degradation rate of one or more immunoglobulins.

In yet another variation, kits for determining the biosynthetic rate or degradation rate of one or more proteins or peptides in an individual are provided. The kit may include labeled water and instructions for use of the kit. The kit may optionally include chemical compounds for isolating proteins from urine, bone, or muscle, as well as one or more tools for administering labeled water. The kits may further include an instrument or instruments for collecting a sample from the subject. Procedures employing commercially available assay kits and reagents will typically be used according to manufacturer defined protocols unless otherwise noted.

BRIEF DESCRIPTION OF THE DRAWINGS

In FIG. 1A, label (*) enters pool A (precursor pool) and pool B (product) is synthesized from A. The replacement rate constant (k) for pool B is revealed by the shape of the rise-to-plateau curve, as shown here for k=0.1, 0.5 and 1.0 d$^{-1}$. The plateau value of labeling reached in pool B will depend upon the fraction of B derived from the precursor pool. Examples of 50% (FIG. 1B) and 100% B (FIG. 1C) deriving from endogenous synthesis are shown.

FIGS. 9A and 9C present data collected from healthy subjects. FIGS. 9B and 9D present data collected from HIV/AIDS patients.

DETAILED DESCRIPTION OF THE INVENTION

Figure 1:
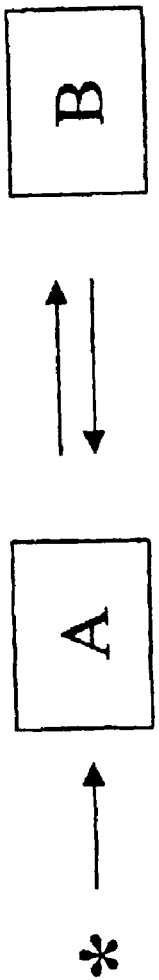
FIG. 1 shows the rise-to-plateau principle shown schematically.
Figure 1:
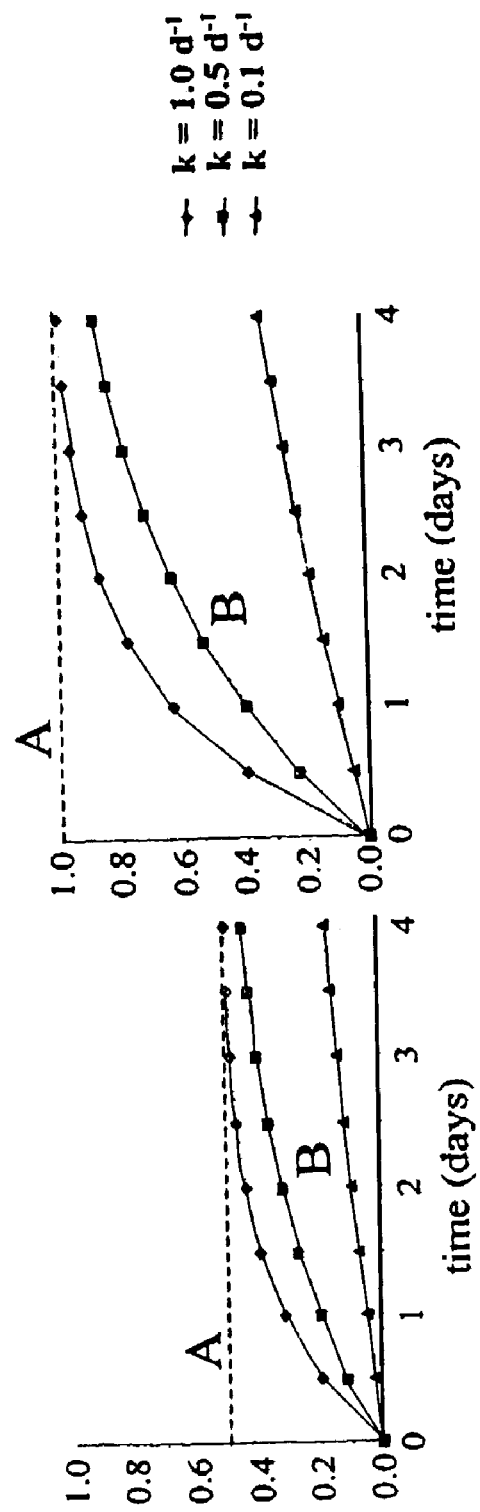

A method for measuring protein synthesis and degradation rates based on intake of labeled water ($^2H_2O$, $^3H_2O$, or $H_2^{18}O$) is described herein. Numerous applications in the fields of medical diagnostics and biological analysis are discussed.

I. General Techniques

The practice of the present invention will employ, unless otherwise indicated, conventional techniques of molecular biology (including recombinant techniques), microbiology, cell biology, biochemistry, immunology, protein kinetics, and mass spectroscopy, which are within the skill of the art. Such techniques are explained fully in the literature, such as, *Molecular Cloning: A Laboratory Manual,* second edition (Sambrook et al., 1989) Cold Spring Harbor Press; *Oligonucleotide Synthesis* (M. J. Gait, ed., 1984); *Methods in Molecular Biology,* Humana Press; *Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993–8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction,* (Mullis et al., eds., 1994); *Current Protocols in Immunology* (J. E. Coligan et al., eds., 1991); *Short Protocols in Molecular Biology* (Wiley and Sons, 1999); and *Mass isotopomer distribution analysis at eight years: theoretical, analytic and experimental considerations* by Hellerstein and Neese (*Am J Physiol* 276 (*Endocrinol Metab.* 39) E1146–E1162, 1999). Furthermore, procedures employing commercially available assay kits and reagents will typically be used according to manufacturer-defined protocols unless otherwise noted.

II. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The general techniques and procedures described or referenced herein are generally well understood and commonly employed using conventional methodology by those skilled in the art, such as, for example, *Mass isotopomer distribution analysis at eight years: theoretical, analytic and experimental considerations* by Hellerstein and Neese (*Am J Physiol* 276 (*Endocrinol Metab.* 39) E1146–E1162, 1999). As appropriate, procedures involving the use of commercially available kits and reagents are generally carried out in accordance with manufacturer defined protocols and/or parameters unless otherwise noted.

"Isotopes" refer to atoms with the same number of protons and hence of the same element but with different numbers of neutrons (e.g., Hydrogen (H) vs. Deuterium (D)).

"Isotopomers" refer to isotopic isomers or species that have identical elemental compositions but are constitutionally and/or stereochemically isomeric because of isotopic substitution, as for $CH_3NH_2$, $CH_3NHD$ and $CH_2DNH_2$.

"Isotopologues" refer to isotopic homologues or molecular species that have identical elemental and chemical compositions but differ in isotopic content (e.g., $CH_3NH_2$ vs. $CH_3NHD$ in the example above). Isotopologues are defined by their isotopic composition, therefore each isotopologue has a unique exact mass but may not have a unique structure. An isotopologue is usually comprised of a family of isotopic isomers (isotopomers) which differ by the location of the isotopes on the molecule (e.g., $CH_3NHD$ and $CH_2DNH_2$ are the same isotopologue but are different isotopomers).

"Mass isotopomer" refers to a family of isotopic isomers that are grouped on the basis of nominal mass rather than isotopic composition. A mass isotopomer may comprise molecules of different isotopic compositions, unlike an isotopologue (e.g., $CH_3NHD$, $^{13}CH_3NH_2$, $CH_3^{15}NH_2$ are part of the same mass isotopomer but are different isotopologues). In operational terms, a mass isotopomer is a family of isotopologues that are not resolved by a mass spectrometer. For quadrupole mass spectrometers, this typically means that mass isotopomers are families of isotopologues that share a nominal mass. Thus, the isotopologues $CH_3NH_2$ and $CH_3NHD$ differ in nominal mass and are distinguished as being different mass isotopomers, but the isotopologues $CH_3NHD$, $CH_2DNH_2$, $^{13}CH_3NH_2$, and $CH_3^{15}NH_2$ are all of the same nominal mass and hence are the same mass isotopomers. Each mass isotopomer is therefore typically composed of more than one isotopologue and has more than one exact mass. The distinction between isotopologues and mass isotopomers is useful in practice because all individual isotopologues are not resolved using quadrupole mass spectrometers and may not be resolved even using mass spectrometers that produce higher mass resolution, so that calculations from mass spectrometric data must be performed on the abundances of mass isotopomers rather than isotopologues. The mass isotopomer lowest in mass is represented as $M_0$; for most organic molecules, this is the species containing all $^{12}C$, $^1H$, $^{16}O$, $^{14}N$, etc. Other mass isotopomers are distinguished by their mass differences from $M_0$ ($M_1$, $M_2$, etc.). For a given mass isotopomer, the location or position of isotopes within the molecule is not specified and may vary (i.e., "positional isotopomers" are not distinguished).

"Mass isotopomer pattern" refers to a histogram of the abundances of the mass isotopomers of a molecule. Traditionally, the pattern is presented as percent relative abundances where all of the abundances are normalized to that of the most abundant mass isotopomer; the most abundant isotopomer is said to be 100%. The preferred form for applications involving probability analysis, however, is proportion or fractional abundance, where the fraction that each species contributes to the total abundance is used (see below). The term isotope pattern is sometimes used in place of mass isotopomer pattern, although technically the former term applies only to the abundance pattern of isotopes in an element.

"Body water enrichment" refers to the percentage of total body water that has been labeled upon administration of labeled water.

A "monomer" refers to a chemical unit that combines during the synthesis of a polymer and which is present two or more times in the polymer.

A "polymer" refers to a molecule synthesized from and containing two or more repeats of a monomer.

An "individual" is a vertebrate, preferably a mammal, more preferably a human. Mammals include, but are not limited- to, humans, farm animals, sport animals, pets, primates, mice and rats.

A "biological sample" encompasses a variety of sample types obtained from an individual. The definition encompasses blood and other liquid samples of biological origin, that are accessible from an individual through sampling by minimally invasive or non-invasive approaches (e.g., urine collection, blood drawing, needle aspiration, and other procedures involving minimal risk, discomfort or effort). The definition also includes samples that have been manipulated in any way after their procurement, such as by treatment with reagents, solubilization, or enrichment for certain components, such as proteins or polynucleotides. The term "biological sample" also encompasses a clinical sample such as serum, plasma, other biological fluid, or tissue samples, and also includes cells in culture, cell supernatants and cell lysates.

"Biological fluid" includes but is not limited to urine, blood, interstitial fluid, edema fluid, saliva, lacrimal fluid, inflammatory exudates, synovial fluid, abcess, empyema or other infected fluid, cerebrospinal fluid, sweat, pulmonary secretions (sputum), seminal fluid, feces, bile, intestinal secretions, or other bodily fluid.

"Labeled Water" includes water labeled with a specific heavy isotope of either hydrogen or oxygen. Specific examples of labeled water include $^2H_2O$, $^3H_2O$, and $H_2^{18}O$.

"Partially purifying" refers to methods of removing one or more components of a mixture of other similar compounds. For example, "partially purifying one or more proteins or peptides" refers to removing one or more proteins or peptides from a mixture of one or more proteins or peptides.

"Isolating" refers to separating one compound from a mixture of compounds. For example, "isolating one or more proteins or peptides" refers to separating one specific protein or peptide from a mixture of one or more proteins or peptides.

III. Methods of the Invention

The invention provides general methods for measuring the synthesis rate of proteins in living systems, including long-lived proteins. The technique is based on the exchange of labeled hydrogen or labeled oxygen atoms from water ($^2H_2O$, $^3H_2O$, or $H_2^{18}O$) into stable, covalent bonds of free amino acids that are subsequently incorporated into proteins.

As a consequence of these unique features of labeled water and protein synthesis, the many technical advantages of a long-term continuous label administration (precursor-product) approach for the measurement of protein synthesis or protein degradation can be exploited without intravenous infusions, medical supervision, special handling needs, sterility concerns, complex instructions, radiation exposure, or high cost. The method is particularly applicable to slow turnover (long-lived) proteins in the body because of the ease with which stable body water enrichments can be maintained over weeks or months.

A. Administration of Labeled Water (i) Theory of $^2H$ or $^3H$-labeled Water Incorporation The theory behind $^2H_2O$ or $^3H_2O$ incorporation is as follows:

(1) $H_2O$ availability is probably never limiting for biosynthetic reactions in a cell (because $H_2O$ represents close to 70% of the content of cells, or >35 Molar concentration), but hydrogen atoms from $H_2O$ contribute stochiometrically to many reactions involved in biosynthetic pathways:

e.g.,:
R—CO—CH$_2$—COOH+NADPH+H$_2$O→R—CH$_2$CH$_2$COOH
(fatty acid synthesis).

As a consequence, label provided in the form of H-labeled water is incorporated into biomolecules as part of synthetic pathways. Hydrogen incorporation can occur in two ways: into labile positions in a molecule (i.e., rapidly exchangeable, not requiring enzyme catalyzed reactions) or into stable positions (i.e., not rapidly exchangeable, requiring enzyme catalysis).

(2) Some of the hydrogen-incorporating steps from cellular water into C—H bonds in biomolecules only occur during well-defined enzyme-catalyzed steps in the biosynthetic reaction sequence, and are not labile (exchangeable with solvent water in the tissue) once present in the mature end-product molecules. For example, the C—H bonds on glucose are not exchangeable in solution. In contrast, each of the following C—H positions exchanges with body water during reversal of specific enzymatic reactions: C-1 and C-6, in the oxaloacetate/succinate sequence in the Krebs' cycle and in the lactate/pyruvate reaction; C-2, in the glucose-6-phosphate/fructose-6-phosphate reaction; C-3 and C-4, in the glyceraldehyde-3-phosphate/dihydroxyacetone-phosphate reaction; C-5, in the 3-phosphoglycerate/glyceraldehyde-3-phosphate and glucose-6-phosphate/fructose-6-phosphate reactions (Katz 1976).

Labeled hydrogen atoms from water ($^2H_2O$ or $^3H_2O$) that are covalently incorporated into specific non-labile positions of a molecule thereby reveals the molecule's "biosynthetic history"—i.e., label incorporation signifies that the molecule was synthesized during the period that $^2H_2O$ or $^3H_2O$ was present in cellular water.

(3) The labile hydrogens (non-covalently associated or present in exchangeable covalent bonds) in these biomolecules do not reveal the molecule's biosynthetic history. Labile hydrogen atoms can be easily removed by incubation with unlabelled water ($H_2O$) (i.e., by reversal of the same non-enzymatic exchange reactions through which $^2H$ or $^3H$ was incorporated in the first place), however:

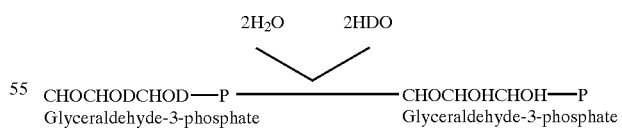

CHOCHODCHOD—P $\xrightarrow{2H_2O \quad 2HDO}$ CHOCHOHCHOH—P
Glyceraldehyde-3-phosphate         Glyceraldehyde-3-phosphate As a consequence, potentially contaminating $^2H$ or $^3H$ label that does not reflect biosynthetic history but is incorporated via non-synthetic exchange reactions, can easily be removed in practice by incubation with natural abundance $H_2O$.

(4) Analytic methods are available for measuring quantitatively the incorporation of labeled hydrogen atoms into biomolecules (e.g., liquid scintillation counting for $^3H$; mass spectrometry or NMR spectroscopy for $^2H$). For further discussions on the theory of labeled water incorporation, see, for example, Jungas 1968.

(ii) Incorporation of Isotopes from Labeled Water into Amino Acids a) Hydrogen Isotopes ($^2H_2O$ and $^3H_2O$)

The hydrogen atoms on C—H bonds are the hydrogen atoms on amino acids that are the most useful for measuring protein synthesis from $^2H_2O$ since the O—H and N—H bonds of peptides and proteins are labile in aqueous solution. As such, the exchange of $^2H$-label from $^2H_2O$ into O—H or N—H bonds occurs without the synthesis of proteins from free amino acids as described above. C—H bonds undergo exchange from $H_2O$ into free amino acids during specific enzyme-catalyzed intermediary metabolic reactions (FIG. 2). The presence of $^2H$-label in C—H bonds of protein-bound amino acids after $^2H_2O$ administration therefore means that the protein was assembled from amino acids that were in the free form during the period of $^2H_2O$ exposure—i.e. that the protein is newly synthesized. Analytically, the amino acid derivative used must contain all the C—H bonds but must remove all potentially contaminating N—H and O—H bonds.

The key question that needs to be answered is the degree of labeling present in C—H bonds of free amino acid or, more specifically, in tRNA-AA, during exposure to $^2H_2O$ in body water. The total number of C—H bonds in each NEAA is known—e.g. 4 in alanine, 2 in glycine, etc. (FIG. 2).

Figure 2A:
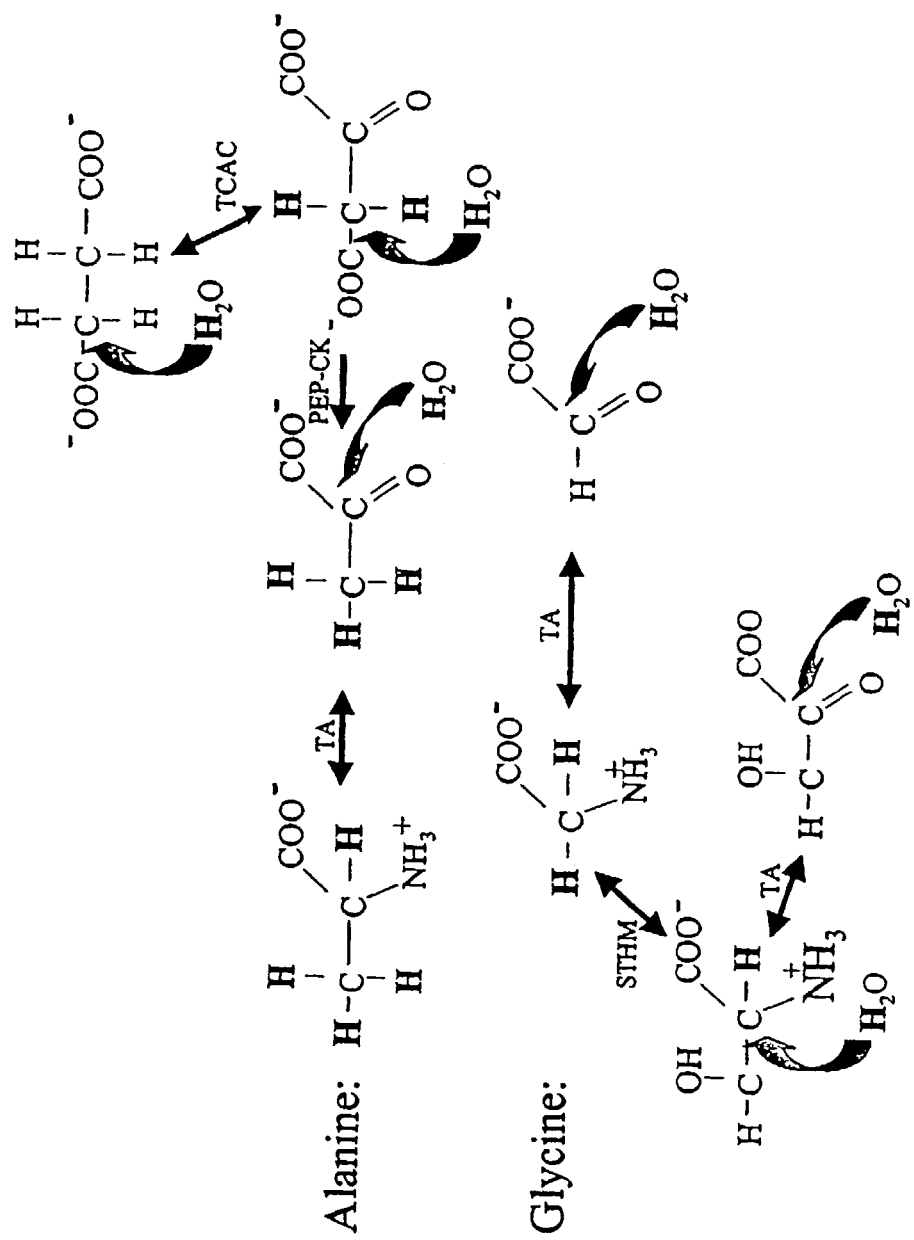
FIGS. 2A–B depict pathways of labeled hydrogen exchange from labeled water into selected free amino acids. Two NEAA's (alanine, glycine) and an EAA (leucine) are shown, by way of example. Alanine and glycine are presented in FIG. 2A. Leucine is presented in FIG. 2B. Abbreviations: TA, transaminase; PEP-CK, phosphoenol-pyruvate carbokinase; TCAC, tricarboxylic acid cycle; STHM, serine tetrahydrofolate methyl transferase.
Figure 2B:
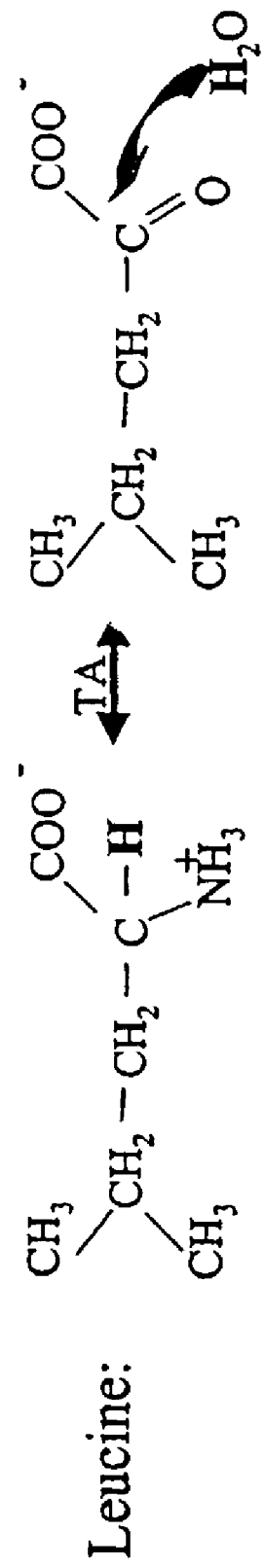

Hydrogen atoms from body water may be incorporated into free amino acids. $^2H$ or $^3H$ from labeled water can enter into free amino acids in the cell through the reactions of intermediary metabolism, but $^2H$ or $^3H$ cannot enter into amino acids that are present in peptide bonds or that are bound to transfer RNA. Free essential amino acids may incorporate a single hydrogen atom from body water into the α-carbon C—H bond, through rapidly reversible transamination reactions (FIG. 2). Free non-essential amino acids contain a larger number of metabolically exchangeable C—H bonds, of course, and are therefore expected to exhibit higher I.E. (isotopic enrichment) values per molecule from $^2H_2O$ in newly synthesized proteins (FIGS. 2A–B).

One of skill in the art will recognize that labeled hydrogen atoms from body water may be incorporated into other amino acids via other biochemical pathways. For example, it is known in the art that hydrogen atoms from water may be incorporated into glutamate via synthesis of the precursor α-ketoglutrate in the citric acid cycle. Glutamate, in turn, is known to be the biochemical precursor for glutamine, proline, and arginine. Other amino acids synthesis pathways are known to those of skill in the art.

b) Oxygen Isotopes ($H_2^{18}O$)

Figure 2C:
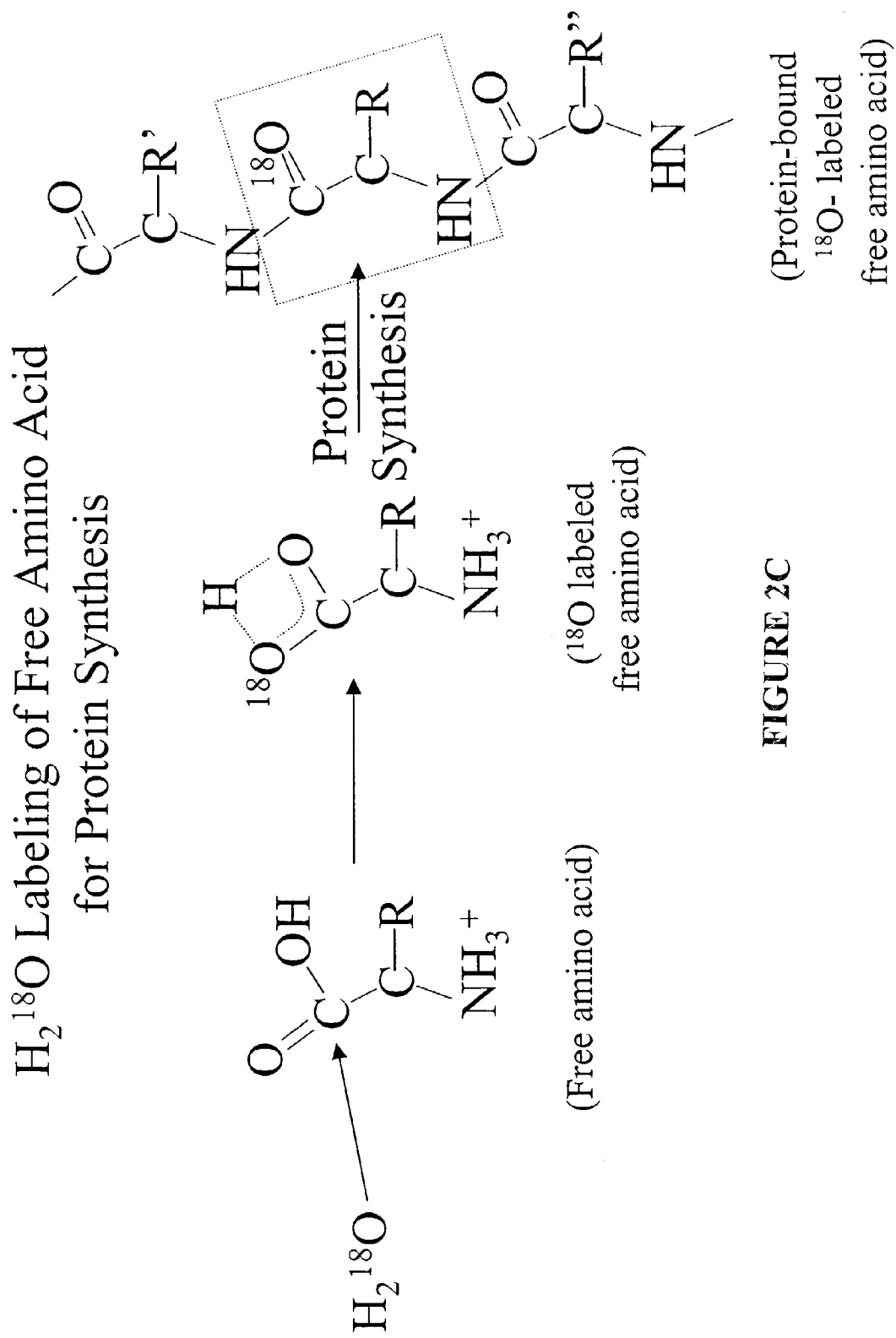
FIG. 2C depicts $H_2^{18}O$ labeling of free amino acids for protein synthesis.

Oxygen atoms may also be incorporated into amino acids through enzyme-catalyzed reactions. For example, oxygen exchange into the carboxylic acid moiety of amino acids may occur during enzyme catalyzed reactions. Incorporation of labeled oxygen into amino acids is known to one of skill in the art as illustrated in FIG. 2C.

B. Determination of Protein Biosynthesis and Degradation Rates

Protein biosynthesis and degradation rates can be determined by two general methods using the techniques of this invention: continuous labeled water administration or discontinuous labeled water administration. For continuous labeled water administration, the following generalized steps may be followed: (a) administering labeled water to an individual over a period of time sufficient to maintain relatively constant water enrichments over time in the individual, wherein the water is labeled with one or more isotopes such as $^2H$, $^3H$, and $^{18}O$; (b) obtaining one or more bodily tissues or fluids from the individual; (c) measuring incorporation of the one or more isotopes into the one or more proteins or peptides; (d) calculating the isotopic enrichment values in the one or more proteins or peptides; and (e) applying a precursor-product relationship to the isotopic enrichment values to determine the biosynthetic rate of the one or more proteins or peptides. Optionally, the proteins or peptides may be partially purified, or fully isolated, from the biological sample sample collected. Furthermore, the component amino acids of the proteins or peptides may be isolated and analyzed.

For the discontinuous labeled water administration, the following generalized steps may be followed: (a) administering labeled water to an individual, wherein the water is labeled with one or more isotopes such as $^2H$, $^3H$, and $^{18}O$; (b) discontinuing the administering step (a); (c) obtaining one or more bodily tissues or fluids from the individual; (d) measuring incorporation of the one or more isotopes into the one or more proteins or peptides; (e) calculating the isotopic enrichment values in the one or more proteins or peptides; and (f) applying an exponential decay relationship to the isotopic enrichment values to determine the degradation rate of the one or more proteins or peptides. Optionally, the proteins or peptides may be partially purified or isolated from the sample. Furthermore, the component amino acids of the proteins or peptides may be isolated and analyzed.

It should be noted that the above steps need not be conducted in the exact order specified. For example, the isotopic enrichment values may be calculated prior isolating bodily tissues or measuring isotopic incorporation into proteins or peptides.

(i) Administering Labeled Water to an Individual

For both methods, labeled water (particularly $^2H_2O$, $^3H_2O$, or $H_2^{18}O$) may be readily obtained commercially. $^2H_2O$ may be purchased from Cambridge Isotope Labs (Andover, Mass.). $^3H_2O$ may be purchased, e.g., from New England Nuclear, Inc. Chemicals and enzymes may be purchased from Sigma, Inc. (St. Louis, Mo.). In general, $^2H_2O$ is non-radioactive and thus, presents less toxicity concerns than radioactive $^3H_2O$. If $^3H_2O$ is utilized, then a non-toxic amount, which is known to those of skill in the art, is administered.

Relatively high body water enrichments of $^2H_2O$ (e.g., 1–5% of the total body water is labeled) have been achieved using the techniques of the invention. This water enrichment is relatively constant and stable as these levels are maintained for weeks or months in humans and in experimental animals without any evidence of toxicity (see FIGS. 3 and 9–10). This finding in a large number of human subjects (>100 people) is contrary to previous concerns about vestibular toxicities at high doses of $^2H_2O$. Applicants have discovered that as long as rapid changes in body water enrichment are prevented (e.g., by initial administration in small, divided doses), high body water enrichments of $^2H_2O$ can be maintained with no toxicities. Previous dosing of $^2H_2O$ in humans, for other purposes (e.g., measurement of fatty acid or cholesterol synthesis or gluconeogenesis) have typically used lower doses and achieved lower body water enrichment. The low expense of commercially available $^2H_2O$ allows long-term maintenance of enrichments in the 1–5% range at relatively low expense (e.g., lower cost for 2 months labeling at 2% $^2H_2O$ enrichment, and thus 7–8% enrichment in the alanine precursor pool (FIGS. 2A–B), than for 12 hours labeling of $^2H$-leucine at 10% free leucine enrichment, and thus 7–8% enrichment in leucine precursor pool for that period).

Relatively high and relatively constant body water enrichments for administration of $H_2{}^{18}O$ may also be accomplished, since the $^{18}O$ isotope is not toxic, and does not present a significant health risk as a result (FIG. 2C).

Administration of labeled water can be achieved in various ways. For the continuous labeling method, sufficient amount of labeled water is administered such that an isotopic plateau value of maximal or isotopic enrichment is approached (i.e. wherein the concentration of labeled water is relatively constant over time). For example, see FIG. 4, *H enrichment v. time. If the continuous labeling period can be maintained for as long as 4–5 half-lives of a protein, the asymptote reached and the shape of the I.E. curve approaching this asymptote will reveal the "true precursor" isotopic enrichment [3] as well as the fractional replacement rate of the protein product (FIG. 1). By labeling to plateau while maintaining a stable precursor pool enrichment, it is thereby possible to overcome the biological complexities of cellular amino acid pools.

In one embodiment, labeled water such as $^2H_2O$ is taken orally (e.g., by drinking via the mouth) intermittently to achieve a relatively constant enrichment in the individual. In another embodiment, labeled water is administered intravenously to achieve a relatively constant water enrichment in the individual. This method of administration avoids frequent oral dosing. In another embodiment, the duration of labeled water exposure is sufficient to characterize the full isotope incorporation curve into the protein approaching its asymptotic value or sufficient to characterize the full isotope incorporation curve into a different, fully or nearly fully turned-over protein. Once daily administration of small amounts of $^2H_2O$ (3–6 ounces/day) allows maintenance of extremely constant levels of $^2H_2O$ enrichment in body water in humans (FIG. 3) and administration in drinking water allows constant levels in animals (FIG. 4) for periods as long as several months or longer. This stability is due to the uniquely slow turnover of the body water pool compared to any other biosynthetic precursor in animals (e.g., half-life of 20 minutes for $^2H$-glucose, <30 minutes for $^2H$-leucine, versus 10–14 days for $^2H_2O$).

For the discontinuous labeling method, an amount of labeled water is measured and then administered, one or more times, and then the exposure to labeled water is discontinued and wash-out of labeled water from body water pool is allowed to occur. The time course of protein degradation may then be monitored.

(ii) Obtaining One or More Bodily Tissues or Fluids from Said Individual

For both continuous labeling and discontinuous labeling methods, a biological sample is obtained from bodily fluids or tissues of an individual. Specific methods of obtaining biological samples are well known in the art. Bodily fluids include, but are not limited to, urine, blood, blood serum, amniotic fluid, spinal fluid, conjunctival fluid, salivary fluid, vaginal fluid, stool, seminal fluid, and sweat. The fluids may be isolated by standard medical procedures known in the art.

One or more proteins or peptides may be obtained, and optionally partially purified or isolated, from the biological sample using standard biochemical methods known in the art. Examples of proteins that may be partially purified or isolated include, but are not limited to, bone collagen, liver collagen, lung collagen, cardiac collagen, muscle myosin, serum hormone, plasma apolipoproteins, serum albumin, clotting factor, immunoglobulin, mitochondrial protein. Peptide fragments of proteins may also be obtained. The frequency of biological sampling can vary depending on different factors. Such factors include, but are not limited to, the nature of the one or more proteins or peptides, ease of sampling, half-life of a drug used in a treatment if monitoring responses to treatment.

For both continuous and discontinuous labeling methods, the one or more proteins and/or peptides may also be purified partially purified, or optionally, isolated, by conventional purification methods including high pressure liquid chromatography (HPLC), fast performance liquid chromatography (FPLC), gas chromatography, gel electrophoresis, and/or any other separation methods.

For both continuous and discontinuous labeling methods, the one or more proteins and/or peptides may be hydrolyzed to form smaller oligopeptides or amino acids. Hydrolysis methods include any method known in the art, including, but not limited to, chemical hydrolysis (such as acid hydrolysis) and biochemical hydrolysis (such as peptidase degradation). Hydrolysis may be conducted either before or after protein and/or peptide purification and/or isolation. The oligopeptides and amino acids also may be partially purified, or optionally, isolated, by conventional purification methods including high- performance liquid chromatography (HPLC), fast performance liquid chromatography (FPLC), gas chromatography, gel electrophoresis, and/or any other methods of separating chemical compounds, proteins, peptides, or amino acids.

(iii) Detecting the Incorporation of One or More Isotopes

For both continuous and discontinuous labeling methods, isotopic enrichment from proteins, peptides or amino acids can be determined by various methods such as mass spectrometry, particularity gas chromatography-mass spectrometry (GC-MS), nuclear magnetic resonance (NMR), or liquid scintillation counting.

Incorporation of labeled isotopes into proteins or peptides may be measured directly. Alternatively, incorporation of labeled isotopes may be determined by measuring the incorporation of labeled isotopes into one or more oligopeptide or amino acid hydrolysis products of peptides and proteins. The hydrolysis products may optionally be measured following either partial purification or isolation by any known separation method, as described previously.

a. Mass Spectrometry

Mass spectrometers convert components of a sample into rapidly moving gaseous ions and separate them on the basis of their mass-to-charge ratios. The distributions of isotopes or isotopologues of ions, or ion fragments, may thus be used to measure the isotopic enrichment in one or more protein, peptide, or amino acid.

Generally, mass spectrometers comprise an ionization means and a mass analyzer. A number of different types of mass analyzers are known in the art. These include, but are not limited to, magnetic sector analyzers, electrostatic analyzers, quadrapoles, ion traps, time of flight mass analyzers, and fourier transform analyzers. In addition, two or more mass analyzers may be coupled (MS/MS) first to separate precursor ions, then to separate and measure gas phase fragment ions.

Mass spectrometers may also include a number of different ionization methods. These include, but are not limited to, gas phase ionization sources such as electron impact, chemical ionization, and field ionization, as well as desorption sources, such as field desorption, fast atom bombardment, matrix assisted laser desorption/ionization, and surface enhanced laser desorption/ionization. In addition, mass spectrometers may be coupled to separation means such as gas chromatography (GC) and high performance liquid chromatography (HPLC). In gas-chromatography mass-spectrometry (GC/MS), capillary columns from a gas chromatograph are coupled directly to the mass spectrometer, optionally using a jet separator. In such an application, the gas chromatography (GC) column separates sample components from the sample gas mixture and the separated components are ionized and chemically analyzed in the mass spectrometer.

When GC/MS is used to measure mass isotopomer abundances of organic molecules such as amino acids, hydrogen-labeled isotope incorporation is amplified 3 to 7-fold. This is because of the nearly linear additive effects of hydrogen-labeling in each labeling location of an amino acid (FIG. 2). As a consequence of this discovery, the sensitivity and efficiency of hydrogen labeling attains to levels comparable to administration of specifically labeled amino acids.

In one embodiment, $^2H$, $^3H$, or $^{18}O$-enrichments of proteins or peptides may be measured directly by mass spectrometry.

In another embodiment, the proteins or peptides may be partially purified, or optionally isolated, prior to mass spectral analysis. Furthermore, the component amino acids of the polypeptides may be purified.

In another embodiment, $^2H$, $^3H$, or $^{18}O$-enrichments of proteins, peptides, amino acids after hydrolysis of a protein or peptide, are measured by gas chromatography-mass spectrometry.

In each of the above embodiments, because of the unique constancy of body labeled water enrichments over time, the synthesis rate of the protein can be calculated by application of the precursor-product relationship using either labeled body water enrichment values or asymptotic isotope enrichment in the relevant amino acid of a fully turned over protein to represent the true precursor pool enrichment. Alternatively, the degradation rate may be calculated using an exponential decay curve.

b. Liquid Scintillation

Radioactive isotopes may be observed using a liquid scintillation counter. Radioactive isotopes such as $^3H$ emit radiation that is detected by a liquid scintillation detector. The detector converts the radiation into an electrical signal, which is amplified. Accordingly, the number of radioactive isotopes in a protein, peptide, or amino acid may be measured.

In one embodiment, the $^3H$-enrichment value in a bodily tissue or fluid may be measured directly by liquid scintillation.

In another embodiment, the proteins or peptides or component amino acids may be partially purified, or optionally isolated, and subsequently measured by liquid scintillation.

In another embodiment $^3H$-enrichments of proteins, peptides, amino acids after hydrolysis of the protein or peptide, are measured by liquid scintillation. In each of the above embodiments, because of the unique constancy of body labeled water enrichments over time, the synthesis rate of the protein can be calculated by application of the precursor-product relationship using either labeled body water enrichment values or asymptotic isotope enrichment in the relevant amino acid of a fully turned over protein to represent the true precursor pool enrichment. Alternatively, the degradation rate may be calculated using an exponential decay curve.

(iv) Determining the Biosynthetic or Degradation Rate a. MIDA: Where p Reflects Body $H_2O$ Enrichment—Calculating the Relationship Between Mass Isotopomer Abundances and p in a Polymer of Known n Biosynthetic and degradation rates may be calculated by combinatorial analysis, by hand or via an algorithm. Variations of Mass Isotopomer Distribution Analysis (MIDA) combinatorial algorithm are discussed in a number of different sources known to one skilled in the art. Specifically, the MIDA calculation methods are the subject of U.S. Pat. No. 5,336,686, incorporated herein by reference. The method is further discussed by Hellerstein and Neese (1999), as well as Chinkes, et al. (1996), and Kelleher and Masterson (1992), all of which are hereby incorporated by reference in their entirety.

In addition to the above-cited references, calculation software implementing the method is publicly available from Professor Marc Hellerstein, University of California, Berkeley.

In brief, calculation of the number (n) of metabolically exchanged H-atoms (between amino acids and cellular water) is by combinatorial analysis, or MIDA. In brief, the relative fraction of double-labeled to single-labeled amino acid molecules reveals n if the precursor pool enrichment of $^2H$, $^3H$, or $^{18}O$ (p) is known. If one assumes that p reflects body labeled water enrichment, then n can be calculated by combinatorial analysis.

Fractional abundances of mass isotopomers result from mixing natural abundance molecules with molecules newly synthesized from a pool of labeled monomers characterized by the parameters. A mixture of this type can be fully characterized by f the fraction new, and p. The algorithm proceeds in step-wise fashion, beginning with the simplest calculation, a molecule synthesized from a single element containing isotopes with the same fractional abundances that occur in nature and not mixed with any other molecules. We then proceed to molecules containing more than one element with all isotopes at natural abundance; then to non-polymeric molecules containing different elements, some of which are in groups whose isotope composition is not restricted to natural abundance but is variable; then to polymeric molecules containing combinations of repeating chemical units (monomers), wherein the monomers are either unlabeled (containing a natural abundance distribution of isotopes) or potentially labeled (containing an isotopically-perturbed element group); and finally to mixtures of polymeric molecules, composed of both natural abundance polymers and potentially labeled polymers, the latter containing combinations of natural abundance and isotopically-perturbed units.

The last-named calculation addresses the condition generally present in a biological system, wherein polymers newly synthesized during the period of an isotope incorporation experiment are present along with pre-existing, natural abundance polymers and the investigator is interested in determining the proportion of each that is present, in order to infer synthesis rates or related parameters.

The calculation may be accomplished for full-length proteins or peptides prior to hydrolysis. Alternatively, the calculation may be conducted for amino acid hydrolysis products (e.g. oligopeptides or amino acids) of the proteins or peptides following hydrolysis.

iv. b. Where Partial Exchange of Labeled H-atoms is Assumed—Calculating Expressing the Relationship Between Mass Isotopomer Abundances and n at a Known p Alternatively, all the potentially exchanging H-atoms in each amino acid (e.g. 2 for glycine, 4 for alanine, 5 for glutamine, etc.) could be assumed to be partially exchanged with water and the isotopic enrichment of the total H-atom pool (p) calculated by MIDA.

The same MIDA algorithms disclosed in (a) above to generate tables expressing the relationship between mass isotopomer abundances and p in a polymer of known n can be used for expressing the relationship between mass isotopomer abundances and n at a known p. Both types of tables are shown for glycine and alanine (Table 1A–C).

TABLE 1A

Example of MIDA tables generated for selected NEAA (alanine and glycine), including two different values of n for alanine.

| p | $M_0$ | $M_1$ | $M_2$ | $EM_1$ | $EM_2$ | Ratio |
|---|---|---|---|---|---|---|
| 0.000 | 0.8944 | 0.0955 | 0.0101 | | | |
| 0.002 | 0.8891 | 0.1003 | 0.0106 | 0.0048 | 0.0005 | 0.1090 |
| 0.004 | 0.8838 | 0.1050 | 0.0111 | 0.0095 | 0.0011 | 0.1112 |
| 0.006 | 0.8786 | 0.1097 | 0.0117 | 0.0142 | 0.0016 | 0.1135 |
| 0.008 | 0.8733 | 0.1144 | 0.0123 | 0.0189 | 0.0022 | 0.1157 |
| 0.010 | 0.8681 | 0.1190 | 0.0129 | 0.0235 | 0.0028 | 0.1180 |
| 0.012 | 0.8629 | 0.1236 | 0.0135 | 0.0281 | 0.0034 | 0.1203 |
| 0.014 | 0.8578 | 0.1281 | 0.0141 | 0.0326 | 0.0040 | 0.1226 |
| 0.016 | 0.8526 | 0.1326 | 0.0147 | 0.0371 | 0.0046 | 0.1249 |
| 0.018 | 0.8475 | 0.1371 | 0.0154 | 0.0416 | 0.0053 | 0.1273 |
| 0.020 | 0.8424 | 0.1415 | 0.0161 | 0.0460 | 0.0060 | 0.1296 |
| 0.022 | 0.8373 | 0.1459 | 0.0167 | 0.0504 | 0.0067 | 0.1319 |
| 0.024 | 0.8323 | 0.1503 | 0.0174 | 0.0548 | 0.0074 | 0.1343 |
| 0.026 | 0.8273 | 0.1546 | 0.0182 | 0.0591 | 0.0081 | 0.1367 |
| 0.028 | 0.8222 | 0.1589 | 0.0189 | 0.0634 | 0.0088 | 0.1390 |
| 0.030 | 0.8173 | 0.1631 | 0.0197 | 0.0676 | 0.0096 | 0.1414 |
| 0.032 | 0.8123 | 0.1673 | 0.0204 | 0.0718 | 0.0103 | 0.1438 |
| 0.034 | 0.8073 | 0.1715 | 0.0212 | 0.0760 | 0.0111 | 0.1462 |
| 0.036 | 0.8024 | 0.1756 | 0.0220 | 0.0801 | 0.0119 | 0.1487 |
| 0.038 | 0.7975 | 0.1797 | 0.0228 | 0.0842 | 0.0127 | 0.1511 |
| 0.040 | 0.7926 | 0.1837 | 0.0236 | 0.0882 | 0.0135 | 0.1535 |
| 0.042 | 0.7878 | 0.1877 | 0.0245 | 0.0922 | 0.0144 | 0.1560 |
| 0.044 | 0.7829 | 0.1917 | 0.0253 | 0.0962 | 0.0152 | 0.1585 |
| 0.046 | 0.7781 | 0.1957 | 0.0262 | 0.1002 | 0.0161 | 0.1609 |
| 0.048 | 0.7733 | 0.1996 | 0.0271 | 0.1041 | 0.0170 | 0.1634 |
| 0.050 | 0.7686 | 0.2034 | 0.0280 | 0.1079 | 0.0179 | 0.1659 |

Alanine, n = 3

TABLE 1B

Example of MIDA tables generated for selected NEAA (alanine and glycine), including two different values of n for alanine.

| p | $M_0$ | $M_1$ | $M_2$ | $EM_1$ | $EM_2$ | Ratio |
|---|---|---|---|---|---|---|
| 0.000 | 0.8944 | 0.0955 | 0.0101 | | | |
| 0.002 | 0.8874 | 0.1019 | 0.0108 | 0.0064 | 0.0007 | 0.1101 |
| 0.004 | 0.8803 | 0.1081 | 0.0115 | 0.0126 | 0.0014 | 0.1135 |
| 0.006 | 0.8734 | 0.1143 | 0.0123 | 0.0188 | 0.0022 | 0.1169 |
| 0.008 | 0.8664 | 0.1205 | 0.0131 | 0.0250 | 0.0030 | 0.1203 |
| 0.010 | 0.8596 | 0.1265 | 0.0139 | 0.0310 | 0.0038 | 0.1237 |
| 0.012 | 0.8527 | 0.1325 | 0.0148 | 0.0370 | 0.0047 | 0.1271 |
| 0.014 | 0.8459 | 0.1384 | 0.0157 | 0.0429 | 0.0056 | 0.1306 |
| 0.016 | 0.8392 | 0.1442 | 0.0166 | 0.0487 | 0.0065 | 0.1341 |
| 0.018 | 0.8325 | 0.1499 | 0.0176 | 0.0544 | 0.0075 | 0.1376 |
| 0.020 | 0.8258 | 0.1556 | 0.0186 | 0.0601 | 0.0085 | 0.1411 |
| 0.022 | 0.8192 | 0.1612 | 0.0196 | 0.0657 | 0.0095 | 0.1446 |
| 0.024 | 0.8127 | 0.1667 | 0.0206 | 0.0712 | 0.0105 | 0.1481 |
| 0.026 | 0.8061 | 0.1722 | 0.0217 | 0.0767 | 0.0116 | 0.1517 |
| 0.028 | 0.7996 | 0.1775 | 0.0228 | 0.0820 | 0.0127 | 0.1553 |
| 0.030 | 0.7932 | 0.1828 | 0.0240 | 0.0873 | 0.0139 | 0.1589 |
| 0.032 | 0.7868 | 0.1881 | 0.0251 | 0.0926 | 0.0150 | 0.1625 |
| 0.034 | 0.7805 | 0.1932 | 0.0263 | 0.0977 | 0.0162 | 0.1661 |
| 0.036 | 0.7741 | 0.1983 | 0.0275 | 0.1028 | 0.0175 | 0.1698 |
| 0.038 | 0.7679 | 0.2033 | 0.0288 | 0.1078 | 0.0187 | 0.1734 |
| 0.040 | 0.7617 | 0.2083 | 0.0301 | 0.1128 | 0.0200 | 0.1771 |
| 0.042 | 0.7555 | 0.2132 | 0.0314 | 0.1177 | 0.0213 | 0.1808 |
| 0.044 | 0.7493 | 0.2180 | 0.0327 | 0.1225 | 0.0226 | 0.1845 |
| 0.046 | 0.7432 | 0.2227 | 0.0340 | 0.1272 | 0.0240 | 0.1882 |
| 0.048 | 0.7372 | 0.2274 | 0.0354 | 0.1319 | 0.0253 | 0.1920 |
| 0.050 | 0.7312 | 0.2320 | 0.0368 | 0.1365 | 0.0267 | 0.1958 |

Alanine, n = 4

TABLE 1C

Example of MIDA tables generated for selected NEAA (alanine and glycine), including two different values of n for alanine.

| p | $M_0$ | $M_1$ | $M_2$ | $EM_1$ | $EM_2$ | Ratio |
|---|---|---|---|---|---|---|
| 0.000 | 0.9045 | 0.0863 | 0.0092 | | | |
| 0.002 | 0.9009 | 0.0896 | 0.0095 | 0.0033 | 0.0003 | 0.0952 |
| 0.004 | 0.8973 | 0.0928 | 0.0098 | 0.0065 | 0.0006 | 0.0963 |
| 0.006 | 0.8937 | 0.0961 | 0.0102 | 0.0098 | 0.0010 | 0.0974 |
| 0.008 | 0.8902 | 0.0993 | 0.0105 | 0.0130 | 0.0013 | 0.0985 |
| 0.010 | 0.8866 | 0.1025 | 0.0108 | 0.0162 | 0.0016 | 0.0996 |
| 0.012 | 0.8831 | 0.1057 | 0.0112 | 0.0194 | 0.0020 | 0.1008 |
| 0.014 | 0.8796 | 0.1089 | 0.0115 | 0.0226 | 0.0023 | 0.1019 |
| 0.016 | 0.8760 | 0.1121 | 0.0119 | 0.0258 | 0.0027 | 0.1030 |
| 0.018 | 0.8725 | 0.1153 | 0.0122 | 0.0289 | 0.0030 | 0.1042 |
| 0.020 | 0.8690 | 0.1184 | 0.0126 | 0.0321 | 0.0034 | 0.1053 |
| 0.022 | 0.8655 | 0.1215 | 0.0130 | 0.0352 | 0.0038 | 0.1065 |
| 0.024 | 0.8620 | 0.1247 | 0.0133 | 0.0383 | 0.0041 | 0.1077 |
| 0.026 | 0.8585 | 0.1278 | 0.0137 | 0.0415 | 0.0045 | 0.1088 |
| 0.028 | 0.8550 | 0.1309 | 0.0141 | 0.0445 | 0.0049 | 0.1100 |
| 0.030 | 0.8515 | 0.1339 | 0.0145 | 0.0476 | 0.0053 | 0.1112 |
| 0.032 | 0.8481 | 0.1370 | 0.0149 | 0.0507 | 0.0057 | 0.1123 |
| 0.034 | 0.8446 | 0.1401 | 0.0153 | 0.0538 | 0.0061 | 0.1135 |
| 0.036 | 0.8412 | 0.1431 | 0.0157 | 0.0568 | 0.0065 | 0.1147 |
| 0.038 | 0.8377 | 0.1461 | 0.0162 | 0.0598 | 0.0069 | 0.1159 |
| 0.040 | 0.8343 | 0.1492 | 0.0166 | 0.0628 | 0.0074 | 0.1171 |
| 0.042 | 0.8308 | 0.1522 | 0.0170 | 0.0658 | 0.0078 | 0.1183 |
| 0.044 | 0.8274 | 0.1551 | 0.0174 | 0.0688 | 0.0082 | 0.1195 |
| 0.046 | 0.8240 | 0.1581 | 0.0179 | 0.0718 | 0.0087 | 0.1207 |
| 0.048 | 0.8206 | 0.1611 | 0.0183 | 0.0748 | 0.0091 | 0.1220 |
| 0.050 | 0.8172 | 0.1640 | 0.0188 | 0.0777 | 0.0096 | 0.1232 |

Glycine, n = 2
Values shown represent fractional abundances, normalized for the sum of the $M_0$ to $M_2$ - mass isotopomers measured. Abbreviations: n, number of exchanging hydrogen atoms in C—H bonds of NEAA (see text). $EM_1$ and $EM_2$ excess fractional abundance of $M_1$ and $M_2$ mass isotopomers, after subtraction of natural abundance (p = 0.000) value. The values of $EM_1$ and $EM_2$ shown here represent maximal values (i.e., f = 100%), or $A_1^\infty$ and $A_2^\infty$ (14); Ratio, ratio of $EM_2/EM_1$. Calculation algorithms are described in detail elsewhere (14). For alanine, n = 3 and n = 4 sample tables are shown. A table for non-integral values of n can also be generated for glycine.

Calculations are for the N-acetyl, n-butyl ester derivative of each amino acid. In practice, these MIDA "training tables" can be used to convert measured mass isotopomer ratios (e.g. excess $M_2$:excess $M_1[EM_2/EM_1]$) into the n or p present; then, using this value of n or p, the asymptotic label achievable in the most abundant mass isotopomer (e.g. $A_1^\infty$) is determined for calculation of fractional synthesis. Sample calculations for the different models (as described above) are shown (Table 1).

Some examples of experimental data are shown for glycine and alanine from bone collagen in an animal (Table 2).

TABLE 2

Representative labeling data in bone collagen from a rat given 4% $^2H_2O$ in drinking water for 3 weeks

|  | $EM_1$ | $EM_2$ | $EM_2/EM_1$ Ratio | Body $^2H_2O$ Enrichment (%) | Calculated n | $A_1^\infty$ | f(%) |
|---|---|---|---|---|---|---|---|
| Protein-bound glycine | 0.0204 | 0.0022 | 0.1078 | 2.6% | 2 | 0.0390 | 52.3 |
| Protein-bound alanine | 0.0395 | 0.0060 | 0.1518 | 2.6% | 4 | 0.0767 | 51.5 |

Experimental results and calculations are shown for bone collagen isolated from a rat after 3 weeks of $^2H_2O$ intake (4%) in drinking water. $EM_1$ and $EM_2$ were measured in alanine and glycine from the collagen hyrolysate, as described in the text. The value of n for alanine and glycine were calculated based on measured body $^2H_2O$ enrichment (2.6%), using table 1. (see text for details). The calculated value of n and measured $^2H_2O$ enrichment were then used to calculate $A_1^\infty$ (asymptotic $EM_1$ value, if 100% new synthesis, ref 14). Comparison of measured $EM_1$ to calculated $A_1^\infty$ allows calculation of fractional synthesis (f).

Alanine $EM_1=0.0395$ and $EM_2=0.0060$ after 3 wk of $^2H_2O$ labeling. Body $^2H_2O$ enrichments were stable at 2.6%. The $EM_2/EM_1$ ratio is 0.1518, which according to table 1 is consistent with n=4 at $^2H_2O=2.6\%$ (model 1). Because the maximal n for alanine (4) is estimated to represent 100% of the measured body $^2H_2O$ enrichment (2.6%) used for p, there is no need to compare different models of incomplete exchange of alanine hydrogen with body $^2H_2O$ (i.e. exchange is complete). The calculated fractional synthesis of bone collagen is 51.5%. Results for glycine from the same animal revealed an $EM_2/EM_1$ ratio of 0.1078 ($EM_2=0.002$, $EM_1=0.024$), consistent with n=4 at $^2H_2O=2.42\%$ (Table 1), and fractional synthesis of 52.8%.

iv. c. Comparison of Methods (a) and (b)

The model disclosed in (a) above generates an estimate of actively exchanging H-atoms (e.g. ¾ for alanine), similar to the approach at Lee et al. The model disclosed in (b) above generates a fraction of each C—H position that has been exchanged with body water (e.g. 75% exchange in all H's in alanine). It turns out that these two models generate very similar kinetic calculations. Based on the calculated n of C—H positions exchanging with body water in each amino acid (AA), a maximal or asymptotic label incorporation into each mass isotopomer ($A_x^\infty$) is then calculated, using the standard MIDA formulae. This asymptotic value represents the denominator for calculating fractional synthesis from label incorporation curves. Confirmation of these MIDA-calculated $A_x^\infty$ values can then be achieved by long-term labeling protocols.

iv. (d) Applying the Precursor Product Relationship

Next, for the continuous labeling method, the isotopic enrichment is compared to asymptotic (i.e., maximal possible) enrichment and the protein or peptide kinetic parameters (e.g., protein biosynthesis rates) are calculated from precursor-product equations. For the discontinuous labeling method, the rate of decline in isotope enrichment is calculated and the protein or peptide kinetic parameters are calculated from exponential decay equations.

The fractional synthesis or replacement rate ($k_s$) of proteins or peptides may be determined by application of the continuous labeling, precursor-product formula:

$$k_s(d^{-1}) = -\left[\ln\left(1 - \frac{AA(\text{protein})_t(I.E.)}{A^\infty(I.E.)}\right)\right] / time(d),$$

where $A^\infty$ represents the asymptotic or plateau value of the amino acid I.E. (isotopic enrichment) possible under the labeling conditions present and AA(protein)$_t$ represents the measured protein-bound amino acid at time t.

Alternatively, the fractional synthesis or replacement rate ($k_s$) of proteins or peptides may be determined by comparing isotope enrichment values of one or more proteins or peptides to either water enrichment values in the individual. For degradation studies, fractional degradation rates ($k_d$) were calculated by the standard exponential decay equation:

$$k_d(d^{-1}) = -\left[\ln\left(\frac{AA(\text{protein})_t(I.E.)}{A(\text{protein})_0(I.E.)}\right)\right] / time(d),$$

where AA(protein)$_0$ represents the measured protein-bound AA at time zero and AA(protein)$_t$ represents the measured protein-bound AA at time t.

Advantages of Labeling of Proteins from Labeled Water

Use of a long-term constant labeled water enrichment approach in fact provides several enormous practical and technical advantages for the measurement of protein synthesis, that had not previously been recognized. These advantages arise because this method allows use of the precursor-product method in its classic, asymptotic form (FIG. 1):

$$S_{B(t)} = S_A(1 - e^{-kt})$$

Figure 3:
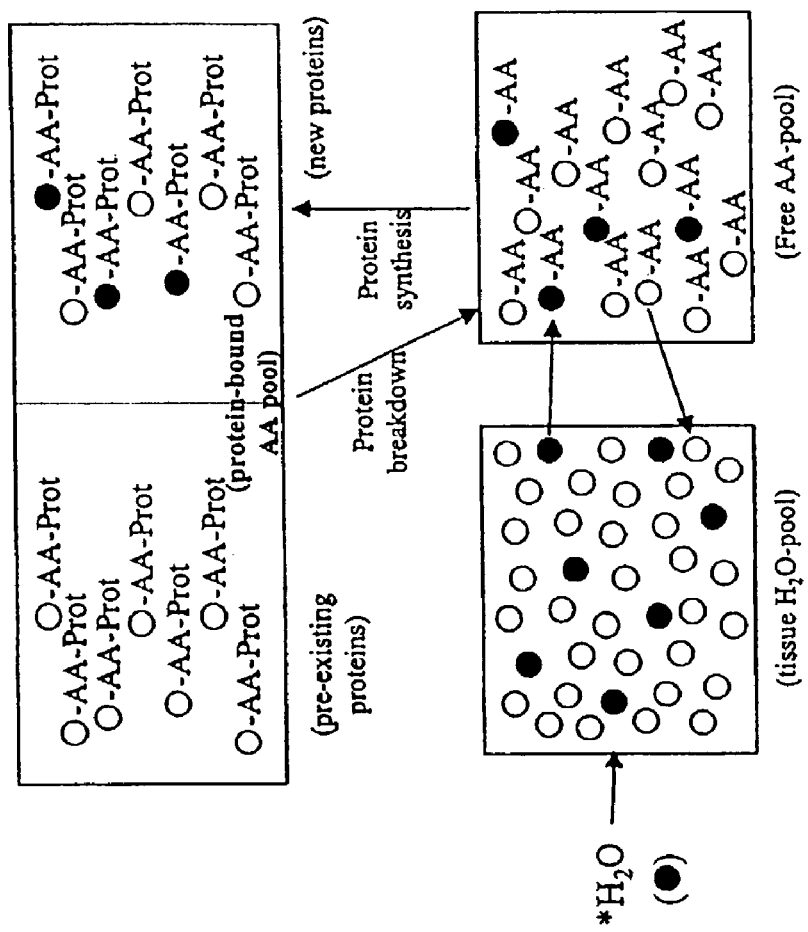
FIG. 3 depicts a schematic model for measurement of new protein synthesis from the incorporation of hydrogen-labeled $H_2O$ (*H) into protein-bound amino acids. Labeled hydrogens are represented by closed circles; unlabeled by open circles.
Figure 4:
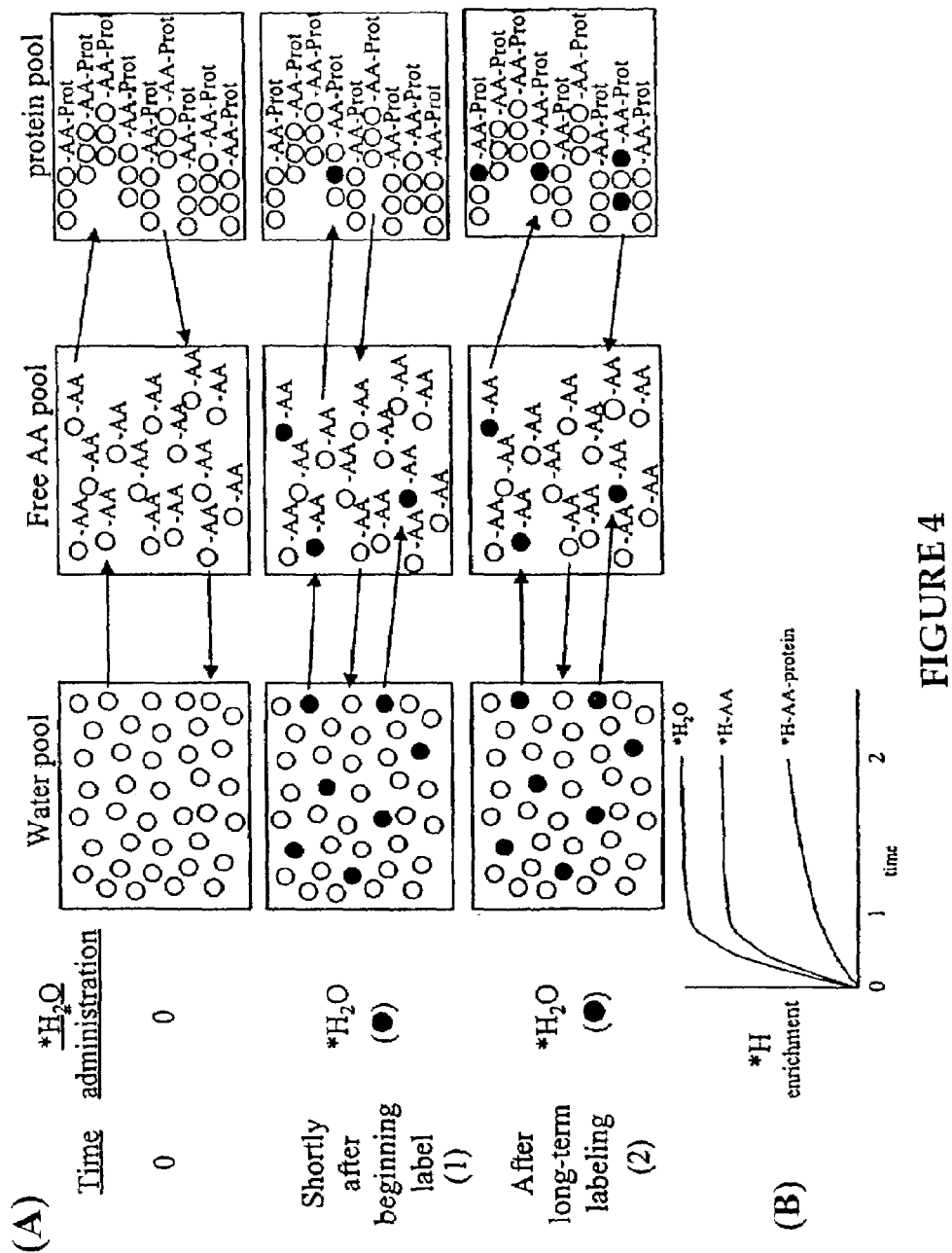
FIG. 4A depicts a schematic model for measurement of new protein synthesis from the incorporation of hydrogen-labeled $H_2O$ (*H) into protein-bound amino acids. Labeled hydrogens are represented by closed circles; unlabeled by open circles. The expected time course of labeling each compartment (body water, free amino acids, protein-bound amino acids) is shown in the inset (FIG. 4B).
Figure 5:
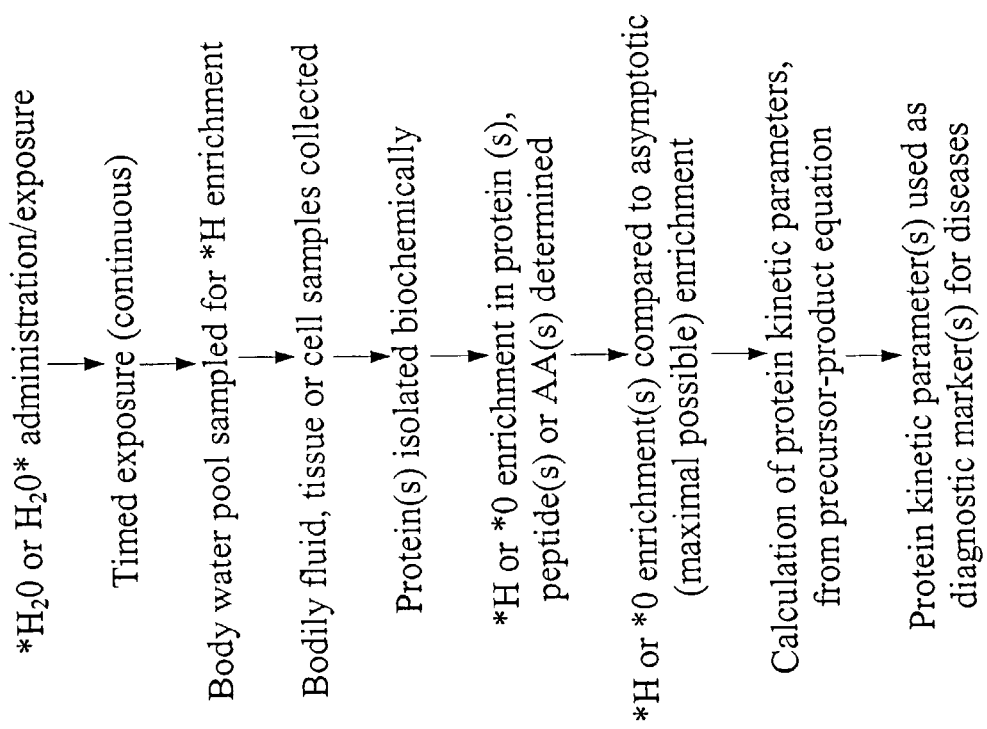
FIG. 5 depicts a flow chart of a method for measuring protein synthesis from incorporation of hydrogen-labeled (*H) or oxygen-labeled (*O) $H_2O$.
Figure 6:
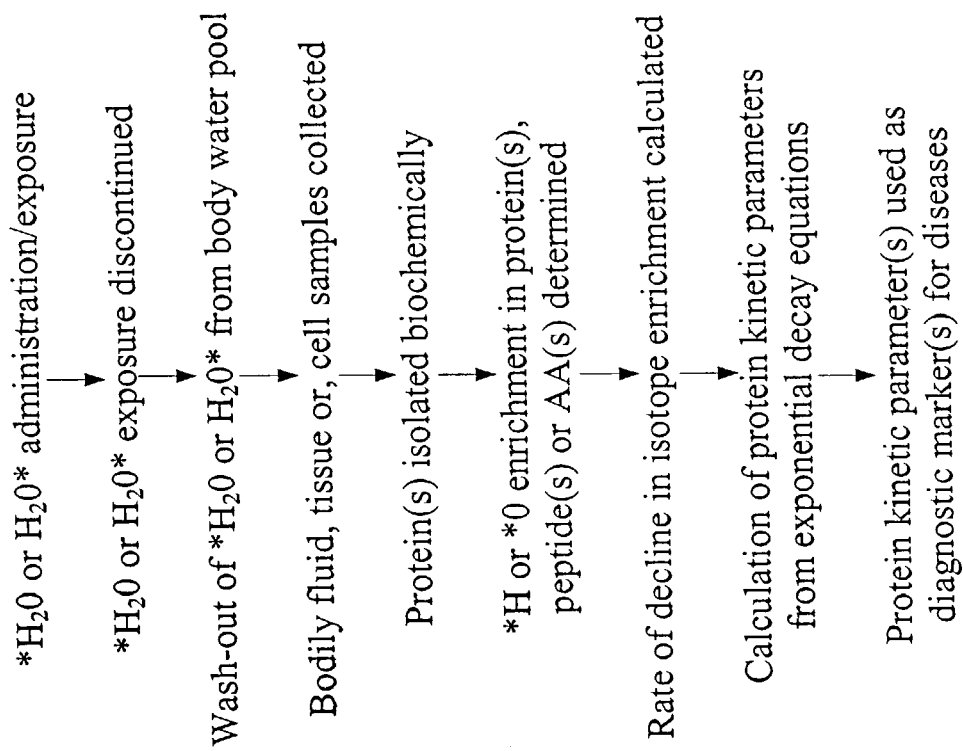
FIG. 6 depicts a flow chart of a method for measuring protein synthesis from the rate of decline (dilution) of labeled hydrogen in protein-bound amino acids, following washout of hydrogen (*H) or oxygen-labeled (*O) $H_2O$.

(1) The option of sampling only one (or a small number) of time points in the product pool is provided, because constant precursor pool enrichments are reliably maintained (FIGS. 3 and 4).

(2) The constant precursor pool enrichments of the "constant infusion" approach are achieved without the need for intravenous infusions or frequent oral dosing regimens, and without the need for medical supervision, complex instructions, special refrigeration or handling needs, sterility testing, etc. Indeed, there can be few if any long-term labeling protocols for human subjects as easy and convenient as drinking a few ounces of water every day or every several days. The ease of this approach represents an enormous operational advantage.

(3) Because of the extreme ease of labeled water administration, the lack of need for medical supervision or facilities, and the low cost of $^2H_2O$ labeling, very long-term labeling protocols (i.e., not just hours or even days, but weeks or months) are permitted. Comparable long-term labeling protocols using specific labeled amino acid precursors are not feasible.

(4) The option of convenient very long-term labeling protocols using this version of the "continuous administration" precursor-product method permits studies of very-slow-turnover proteins, which include some of the most important and interesting proteins in the body, such as bone collagen (the key factor in osteoporosis), muscle myosin (the key factor in strength and rehabilitation therapy), immunoglobulins (the basis of humoral immunity), etc. These studies would not be feasible or affordable in humans using a rapidly turning-over labeled precursor molecule, such as a labeled amino acid.

(5) The option of long-term labeling protocols using the "continuous administration" precursor-product method permits full characterization of the product labeling curve up to the plateau or asymptotic labeling values, thereby overcoming the central methodologic problem of alternative label incorporation studies for protein biosynthesis (problems in estimating the true precursor pool enrichment, Waterlow 1979). Documenting the actual asymptotic value attained is the most rigorously correct solution, in principle, to the problem of the true precursor pool, and this solution becomes available with the labeled water administration method (FIGS. 2, 3 and 4).

(6) Costs are several orders of magnitude lower than equivalent long-term labeling with specific amino acids (e.g., 1L of $^2H_2O$ given over 6 weeks at a cost of about $170 is equivalent to several kg of $^2H$ or $^{13}C$ labeled alanine or glycine to achieve the same isotopic enrichments for 6 weeks, at a cost of many thousands of dollars.

(7) Incorporation of labeled isotopes (e.g. $^2H$, $^3H$, and $^{18}O$) from labeled water into amino acids is highly reproducible. For example, incorporation of $^2H$ from $^2H_2O$ into the C—H bonds of the NEAA studied (alanine or glycine) was highly reproducible (Table 1). The derivatization procedure, combined with the isolation procedure of AA's and proteins, which involves incubation in aqueous solution, removes labile hydrogens present in O—H and N—H bonds. The long period of labeled water administration allows sufficient time for consistent incorporation into both C-2 and other positions of NEAA's to occur. Mass isotopomer analysis confirmed the near-complete exchange of C—H positions in NEAA's such as alanine and glycine. Thus, administration of labeled water in essence results in as reliable labeling as continuous administration of exogenously labeled AA's.

(8) The capacity to achieve 1–2% body water enrichments in humans as well as rodents without toxicities or side-effects, combined with the amplification factor introduced by multiple sites of potential hydrogen entry (FIG. 2), and the analytic precision and sensitivity of mass spectrometers, makes labeling amino acids via labeled water a very efficient, rather than an inefficient, approach. Label incorporation curves can be precisely characterized even at relatively low body water enrichments (e.g. 0.25–0.50%). It is worth pointing out that the amplification factor derives from multiple C—H bonds being potentially labeled and only applies for mass isotopomer analysis of intact AA molecules, i.e. not for radioactivity measurements or for combustion/isotope ratio approaches.

(9) The ease of oral labeled water administration obviates the need for intravenous infusions, medical supervision, sterility concerns, special handling of tracers, or complex instructions. Field studies are made practical, even for long-lived proteins.

(10) The unique constancy of body labeled water enrichments over time (FIG. 10), due to the large and slowly turning over body water pool, makes this approach ideal for application of the rise-to-plateau or precursor-product relationship to slowly turning over proteins. Combined with the extreme ease of oral labeled water administration and the relatively low cost of labeled water (e.g. $^2H_2O$), very slow turnover proteins can be studied by this technique. Our measurements of bone collagen synthesis (FIGS. 13 and 14) and mixed muscle protein synthesis (FIG. 15) are examples of this application.

(11) The ease and low cost of continuous labeling with labeled water, especially $^2H_2O$, permits full exploitation of the rise-to-plateau approach, because constant water labeling is feasible for >4–5 half-lives of almost any protein of interest. This is apparent in the studies of bone collagen synthesis. Variable dilution within tRNA-AA pools [1–5] is overcome by tracing the product labeling curve up to its plateau value (FIG. 1). This possibility represents an important theoretical advantage over most alternative attempts to estimate tRNA-AA (true precursor) enrichments (Waterlow, 1978).

IV. Methods of Use

Using the methods disclosed herein, protein kinetic parameters such as protein biosynthesis or degradation rates can be determined from any number of protein in an individual. These rates can be applied for diagnostic and/or monitoring uses. Many research and clinical applications of this technique can be envisioned, including determining synthesis and turnover rates of medically important proteins such as muscle or cardiac myosin; bone, liver, lung or cardiac collagen; serum hormones; plasma apolipoproteins; serum albumin, clotting factors, and other proteins; immunoglobulins; mitochondrial proteins.

Other uses include, but are not limited to, measurement of bone collagen synthesis as an index of osteoporotic risk, measurement of bone collagen synthesis to monitor responses to hormone replacement therapy, both of which are based on the incorporation of isotopes from labeled water into amino acids in bone collagen. Synthesis of tissue collagen can be used as a measure of fibroproliferative rate in disorders such as liver cirhosis, interstitial lung disease, congestive heart failure, sclerodoma, coal miner's pneumonia (black lung), kidney fibrosis, and other diseases of fibrogenesis and fibrolysis. Response to anti-fibrotic agent therapy can be monitored by the change in tissue collagen synthesis. A patient's progress after treatment with a hypolipidemic agent can be monitored by measuring apolipoprotein B synthesis (e.g., an HMG-CoA reductase inhibitor), based on the incorporation of isotopes from labeled water into alanine or other amino acids in apolipoprotein B. An individual's response to an exercise training or medical rehabilitation regimen can be monitored by measuring the synthesis and breakdown rates of muscle proteins, based on the incorporation of isotopes from labeled water into amino acids in muscle proteins. An index of hypertrophy versus hyperplasia can be determined by measuring the ratio of protein: DNA synthesis rates in a tissue. The presence and/or titer of specific immunoglobulins after vaccination or after an infectious exposure can be determined by measuring the synthesis rate of specific immunoglobulins, based on the incorporation of isotopes from labeled water into immunoglobulin subpopulations.

In another aspect, the invention provides kits for analyzing protein synthesis rates in vivo. The kits may include labeled water (particularly $^2H_2O$, $^3H_2O$, and $H_2^{18}O$ labeled water or a combination thereof), and in preferred embodiments, chemical compounds known in the art for isolating proteins from urine, bone, or muscle and/or chemicals necessary to get a tissue sample, automated calculation software for combinatorial analysis, and instructions for use of the kit.

Other kit components, such as tools for administration of water (e.g., measuring cup, needles, syringes, pipettes, IV tubing), may optionally be provided in the kit. Similarly, instruments for obtaining samples from the subject (e.g., specimen cups, needles, syringes, and tissue sampling devices may also be optionally provided.

V. Literature Citations

1. Airhart, J., A. Vidrich, and E. A. Khairallah. Compartmentation of free amino acids for protein synthesis in rat liver. *Biochem J* 140: 539–45, 1974.
2. Bonotto, S., I. Ndoite, G. Nuyts, E. Fagniart, and R. Kirchmon. Study of the distribution and biological effects of $^3H$ in the Algae Acetabularia, Chlamydomonas and Porphyra. *Curr Top Rad Quart* 12: 115–132, 1977.
3. Etnier, E., C. Travis, and D. Hetrick. Metabolism of organically bound tritium in man. *Rad Res* 100: 487–502, 1984.
4. Hellerstein, M. Methods for measurement of polymerization biosynthesis: three general solutions to the problem of the "true precursor". *Diabetes, Nutrition and Metabolism* In Press, 2000.
5. Hellerstein, M. K., and R. A. Neese. Mass isotopomer distribution analysis at eight years: theoretical, analytic, and experimental considerations. *Am J Physiol* 276: E1146–62, 1999.
6. Hellerstein, M. K., and R. A. Neese. Mass isotopomer distribution analysis: a technique for measuring biosynthesis and turnover of polymers. *Am J Physiol* 263: E988–1001, 1992.
7. Humphrey, T., and D. Davies. A new method for the measurement of protein turnover. *Biochem J* 148: 119–127, 1975.
8. Humphrey, T., and D. Davies. A sensitive method for measuring protein turnover based on the measurement of 2-$^3H$-labeled amino acids in proteins. *Biochem J* 156: 561–568, 1976.
9. Jungas, R. L. Fatty acid synthesis in adipose tissue incubated in tritiated water. *Biochemistry* 7: 3708–17, 1968.
10. Katz, J., and R. Rognstad. Futile cycles in the metabolism of glucose. *Curr Top Cell Regul* 10: 237–89, 1976.
11. Khairallah, E. A., and G. E. Mortimore. Assessment of protein turnover in perfused rat liver. Evidence for amino acid compartmentation from differential labeling of free and tRNA-gound valine. *J Biol Chem* 251: 1375–84, 1976.
12. Mather-Devré, R., and J. Binet. Molecular aspects of tritiated water and natural water in radiation biology. *Prog Biophys Molec Biol* 43: 161–193, 1984.
13. Mewissen, D., M. Furedi, A. Ugarte, and J. Rust. Comparative incorporation of tritium from tritiated water vs tritiated thymidine, uridine or leucine. *Curr Top Rad Res. Quart* 12: 225–254, 1977.
14. Waterlow, J. C., P. J. Garlick, and D. J. Millward, eds. 1978. Protein Turnover in Mammalian Tissues and in the Whole Body. North Holland, Amsterdam.
15. Patterson, B. W., and R. R. Wolfe. Concentration dependance of methyl-palmitate isotope ratios by electron impact ionization gas chromatography/mass spectrometry. *Bioi. Mass Spectrom.* 22: 481–486, 1993.
16. Kelleher, J. K., and T. M. Masterson. Model equations for condensation biosynthesis using stable isotopes and radioisotopes. *Am. J. Physiol.* 262 (*Endocrinol. Metab.* 25): E118–E125, 1992.
17. Chinkes, D. L., A. Aarsland, J. Rosenblatt, and R. R. Wolfe. Comparison of mass isotopomer dilution methods used to calculate VLDL production in vivo. *Am. J. Physiol.* 271 (*Endocrinol. Metab.* 34): E373–E383, 1996.

EXAMPLES

Example 1

$^2H_2O$ Labeling in Rat

Sprague-Dawley rats (200–250 g, Simonsen Inc., Gilroy Calif.) and C57Blk/6ksj mice (10–15 g, Jackson Laboratories, Bar Harbor Me.) were used. Housing was in individual cages for rats and groups of 5 for mice. Feeding was ad-libitum with Purina® rodent chow. All studies received prior approval from the UC Berkeley Animal Care and Use Committee.

The $^2H_2O$ labeling protocol consisted of an initial intraperitoneal (ip) injection of 99.9% $^2H_2O$, to achieve ca. 2.5% body water enrichment (assuming total body water to be 60% of body weight) followed by administration of 4% $^2H_2O$ in drinking water. For labeling of rats in utero, 4% drinking water was started while the male and female adult rats were housed together for mating (i.e. before pregnancy) and the 4% $^2H_2O$ drinking water was continued through the pregnancy and post-delivery period.

Urine was collected longitudinally from some animals to establish the time course of body $^2H_2O$ enrichments. A de-labeling protocol was also carried out in some animals, to monitor label die-away in body water and in proteins. After completing 8–10 weeks of $^2H_2O$ labeling, the 4% $^2H_2O$ was replaced with unlabeled drinking water. Rats were then sacrificed weekly, to establish the time course of body water enrichment and muscle protein labeling. The de-labeling period was for 6 weeks.

Ovariectomy was performed in adult female rodents as described (9). After allowing 3 weeks for recovery from surgery, the rats received either estradiol by subcutaneous pellet (200 µg) or sham placement of pellet. $^2H_2O$ labeling was initiated at the time of pellet placement and continued for 2 weeks, at which time the animals were sacrificed and bone was collected.

Example 2

Incorporation of $^2H_2O$ in Rat Muscle

Figure 7:
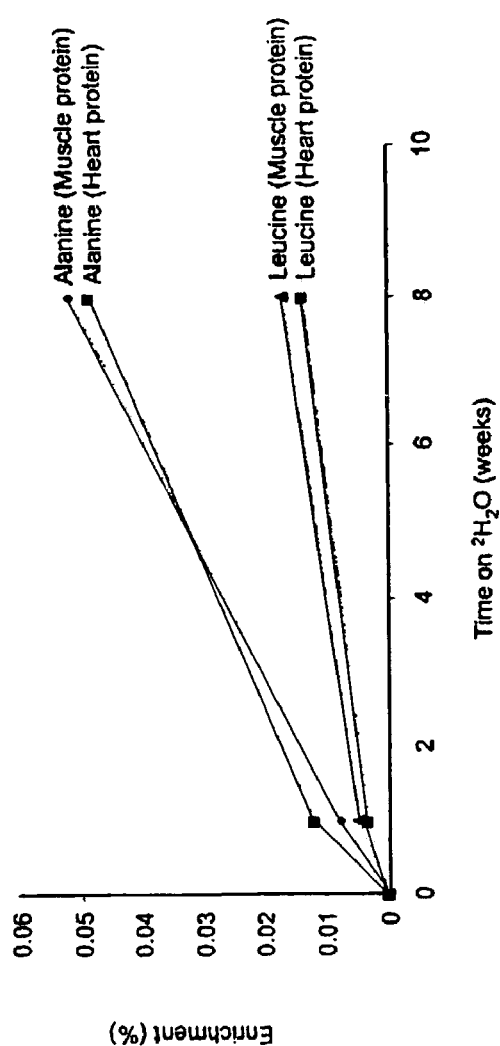
FIG. 7 depicts measured incorporation of $^2H_2O$ into alanine and leucine isolated from rat muscle and heart proteins.

FIG. 7 depicts measured incorporation of $^2H_2O$ into selected amino acids isolated from muscle proteins in the rat. Enrichments of $^2H$ in amino acids was determined by gas chromatographic-mass spectrometric analysis after hydrolysis of muscle proteins to free amino acids.

Example 3

Incorporation of $^2H_2O$ in Rat Bone Collagen

Figure 8:
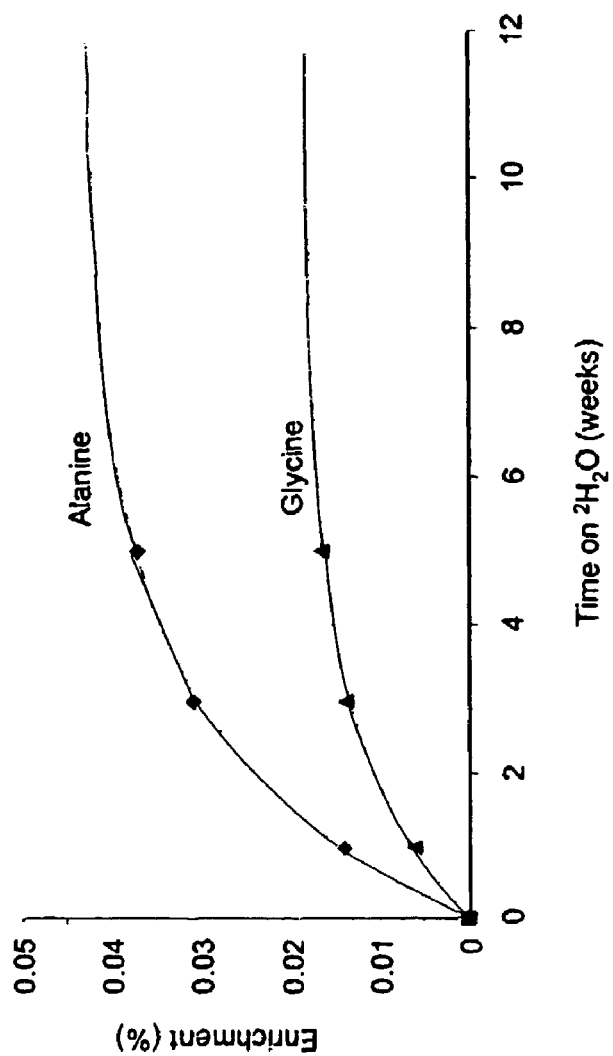
FIG. 8 depicts measured incorporation of $^2H_2O$ into alanine and leucine isolated from rat bone collagen.

FIG. 8 depicts measured incorporation of $^2H_2O$ into selected amino acids isolated from bone collagen in the rat. Enrichment of $^2H$ in amino acids was determined by gas chromatographic-mass spectrometric analysis after hydrolysis of bone collagen to free amino acids. Calculated collagen turnover rate constant (k) was nearly identical from glycine (k=0.044 d$^{-1}$), alanine (k=0.041 d$^{-1}$), or proline (not shown, k=0.038 d$^{-1}$).

Rats were killed every 1–2 weeks during a 10-week period of $^2H_2O$ administration. The rear left femur was collected and was dissected free of soft tissue. Bone marrow and trabecular bone were removed using a needle with sharp cutting surface (ref: Bone 2000). After washing 3 times with water, the bone was splintered and powdered under liquid $N_2$ in a Spex mill and defatted with chloroform:methanol (1:1, v:v). After drying, the powdered bone was subjected to acid hydrolysis in 6N HCl (110° C., 24 hr). The free AA were dried under $N_2$ gas and derivatized for analysis by gas chromatography/mass spectrometry (GC/MS).

Example 4

Incorporation of $^2H_2O$ in Humans

Figure 9:
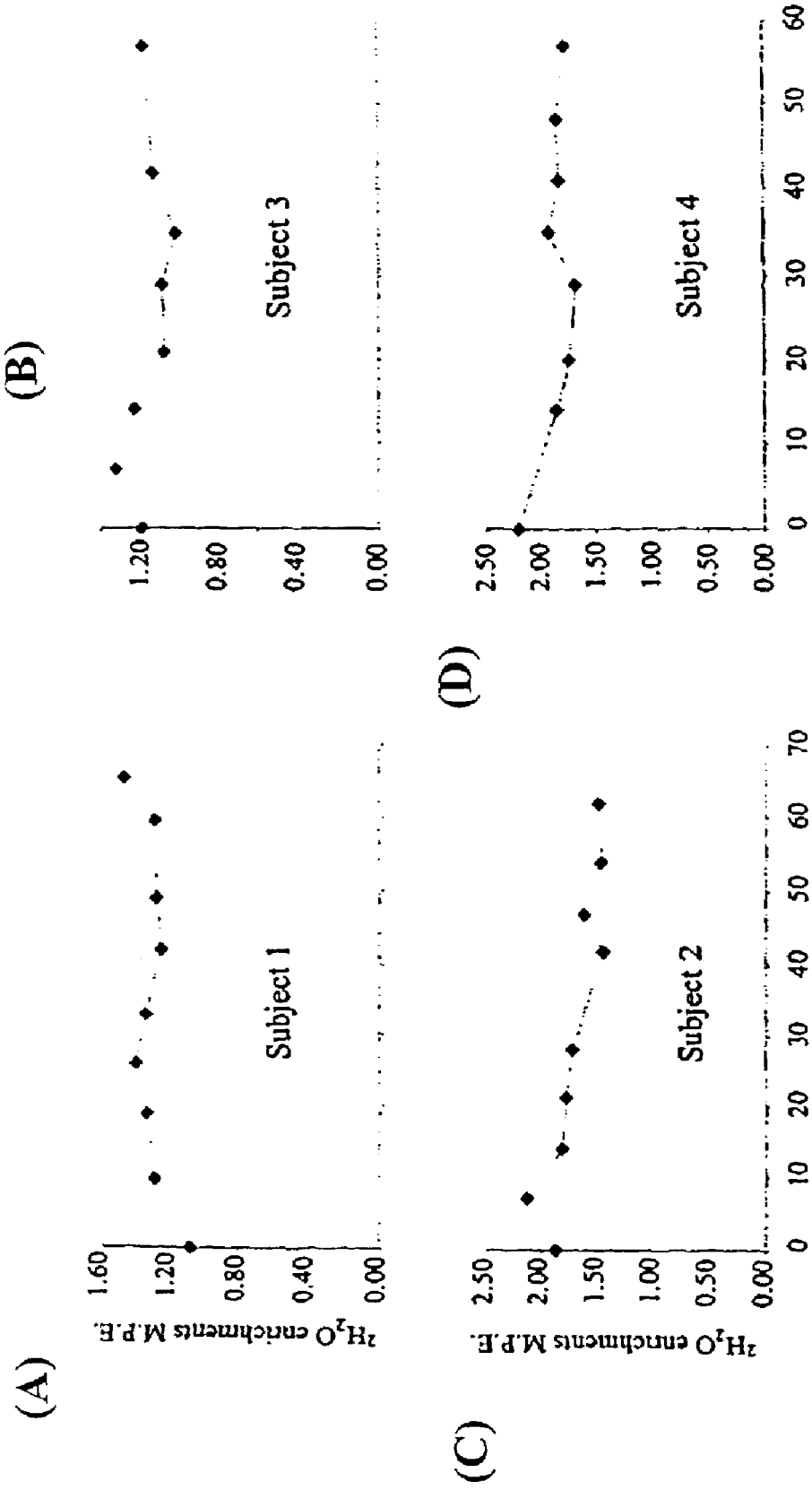
FIG. 9 depicts enrichments of $^2H_2O$ in body water of human subjects who drank 50–100 ml of $^2H_2O$ daily for 10–12 weeks. The data show that the precursor pool of body water is stable over a period of weeks for each subject.

FIG. 9 depicts enrichments of $^2H_2O$ in body water of human subjects who drank 50–100 ml of $^2H_2O$ daily for 10–12 weeks. Left, healthy subjects; right, HIV/AIDS patients. No adverse effects or toxicities were observed in any subjects. Body $^2H_2O$ enrichments were measured by a gas chromatographic-mass spectrometric technique. Constant water enrichment levels over time were observed for each patient.

Example 5

Incorporation of $^2H_2O$ in Body Water of Rats

Figure 10:
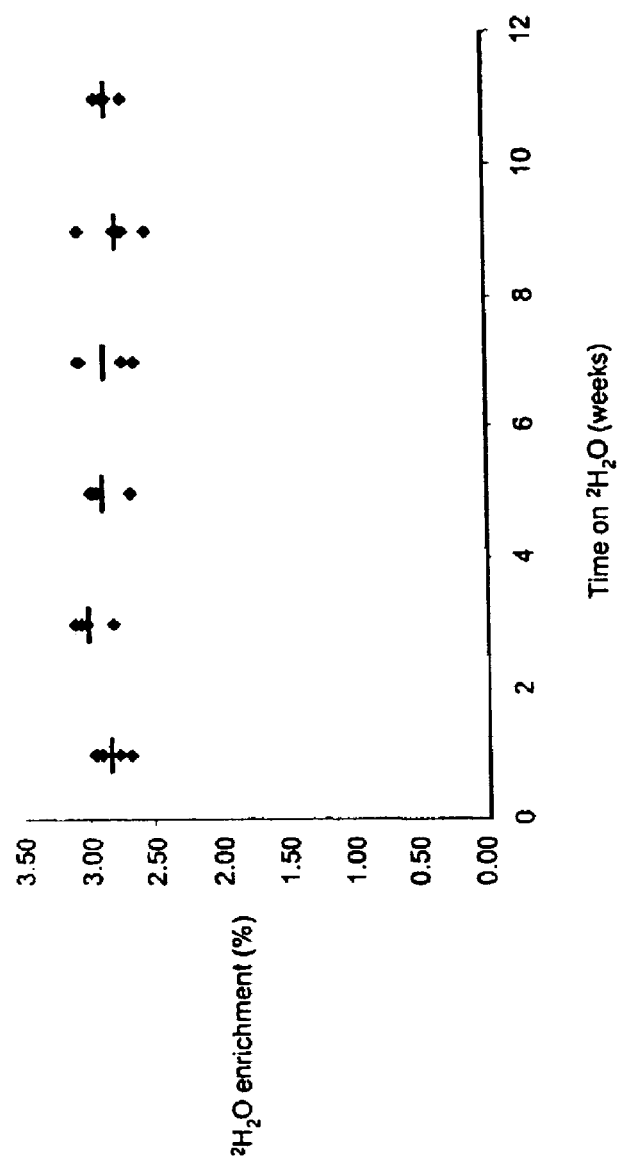
FIG. 10 depicts a time course of body $^2H_2O$ enrichments in rats maintained on 4% drinking water after baseline priming bolus to 2.5–3.0% body water enrichment.

FIG. 10 depicts the enrichment of $^2H_2O$ in body water of rats given 4% $^2H_2O$ as drinking water. Animals grew normally and exhibited no signs of toxicity. Body $^2H_2O$ enrichments were measured by GC/MS.

Figure 13:
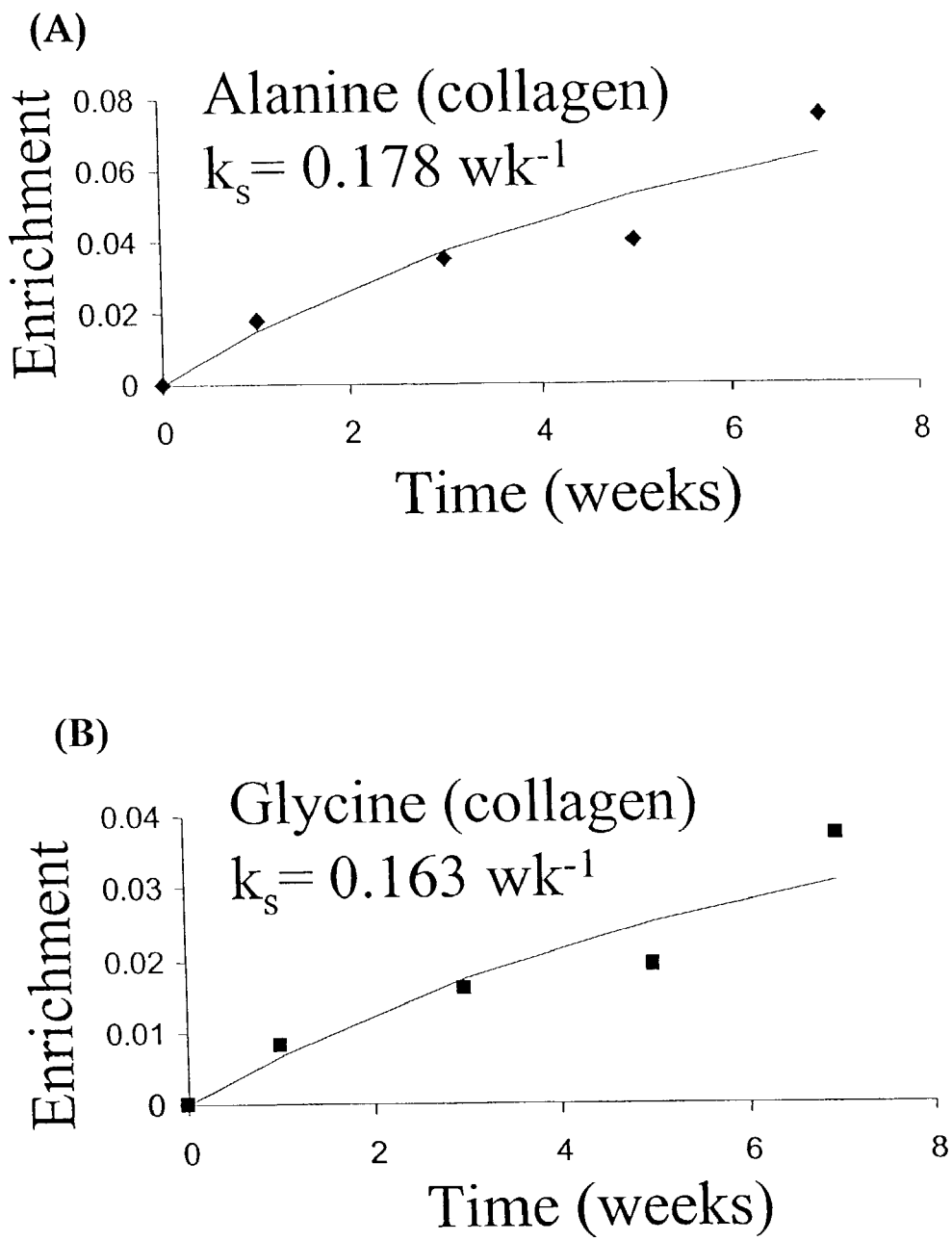
FIG. 13A depicts label incorporation curves into alanine isolated from bone collagen in adult female rats.
FIG. 13B depicts label incorporation curves into glycine isolated from bone collagen in adult female rats. Calculated rate constants for bone collagen synthesis are shown.
Figure 14:
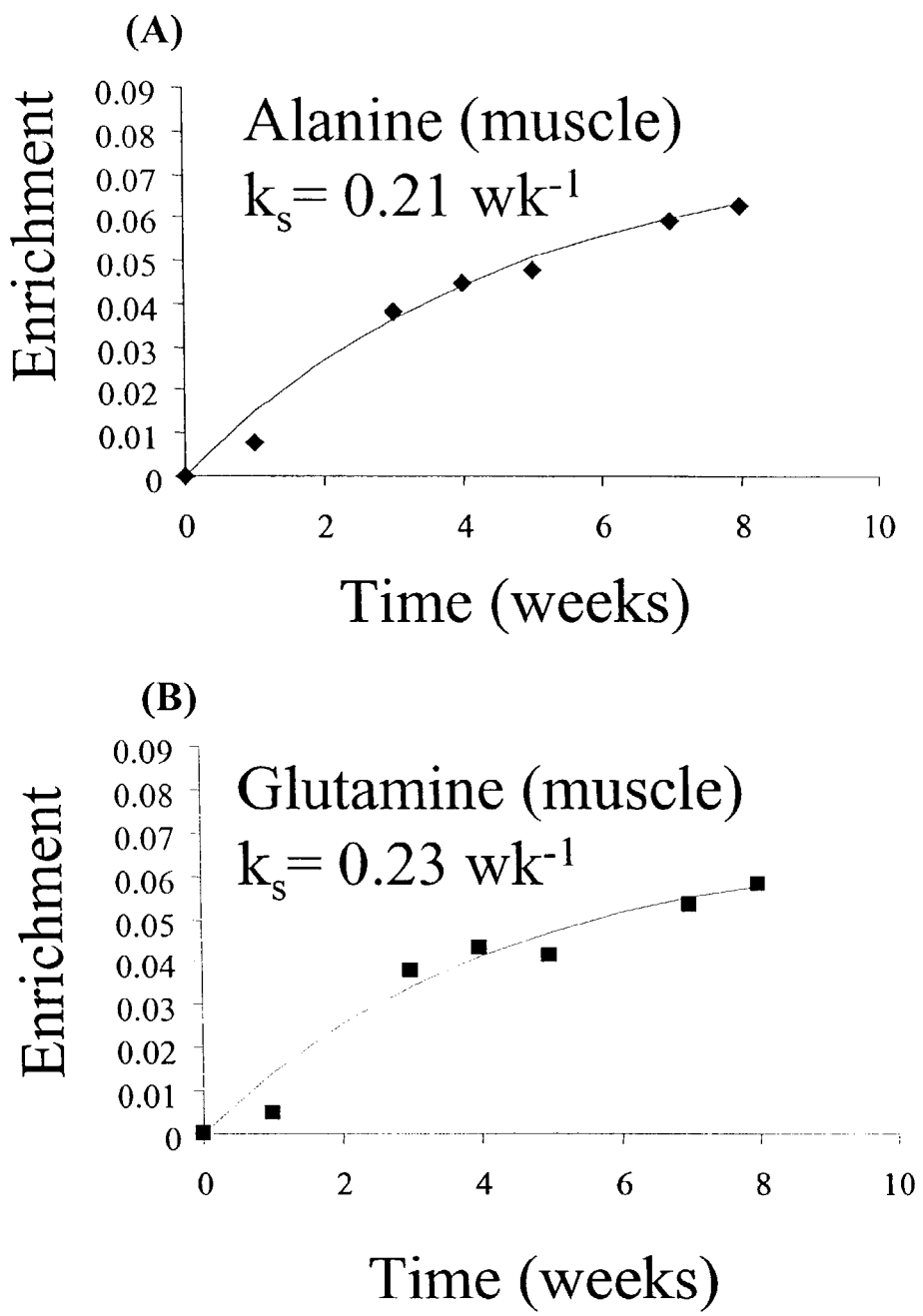
FIG. 14A depicts label incorporation curves into alanine isolated from skeletal muscle proteins in adult female rats.
FIG. 14B depicts label incorporation curves into glutamine isolated from skeletal muscle proteins in adult female rats.
FIG. 14C depicts label incorporation curves into alanine isolated from heart muscle proteins in adult female rats. Calculated rate constants for protein synthesis are shown.
Figure 14:
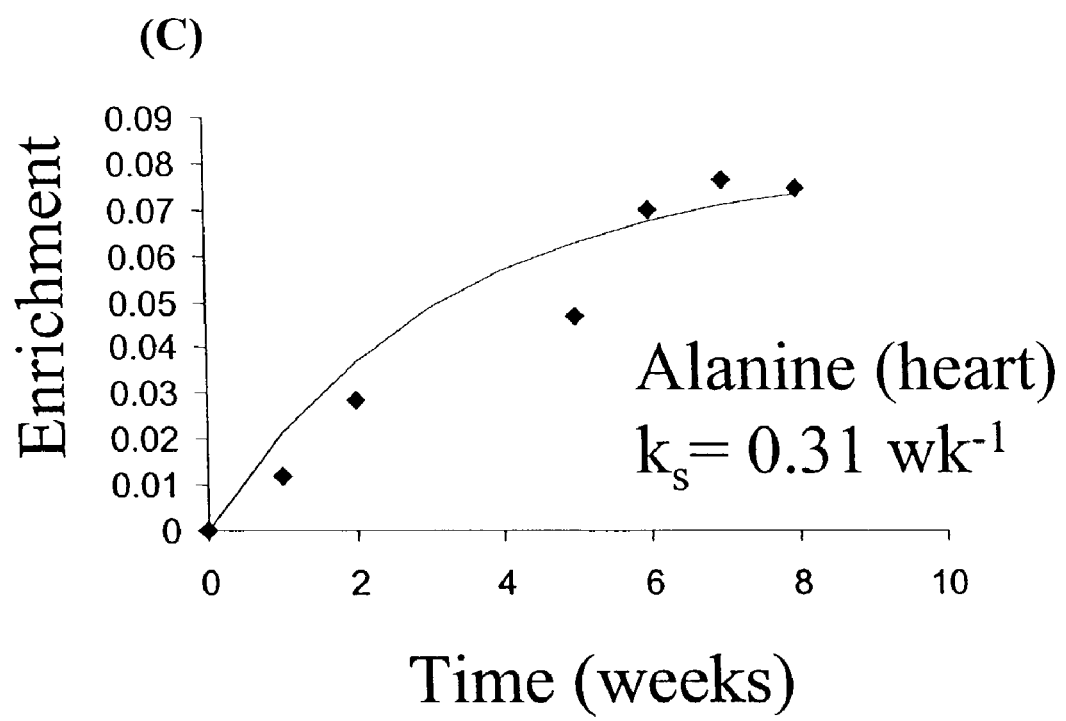

The time course of $^2H$ incorporation from $^2H_2O$ into AA's from bone collagen was measured in growing, adult mice (FIG. 13). The rate constant for rise to plateau ($k_s$) was similar for the NEAA tested (e.g. $k_{s(ala)}$=0.178 wk$^{-1}$, $k_{s(glyc)}$=0.163 wk$^{-1}$).

Example 6

Discontinuous $^2H_2O$ Administration in Rats

Figure 11:
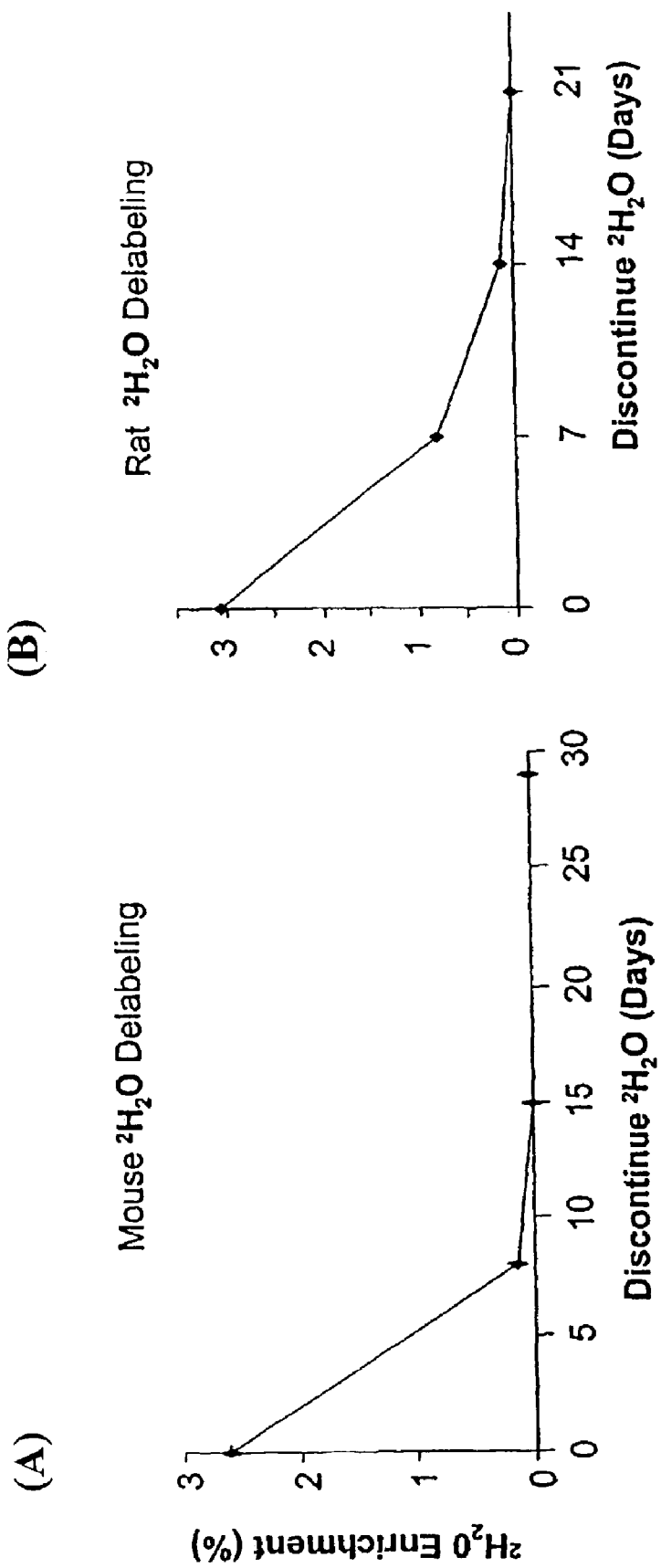
FIG. 11A depicts a washout of $^2H_2O$ from body $^2H_2O$ in mice after discontinuing $^2H_2O$ administration in drinking water.
FIG. 11B depicts a washout of $^2H_2O$ from body $^2H_2O$ in rats after discontinuing $^2H_2O$ administration in drinking water.
Figure 15:
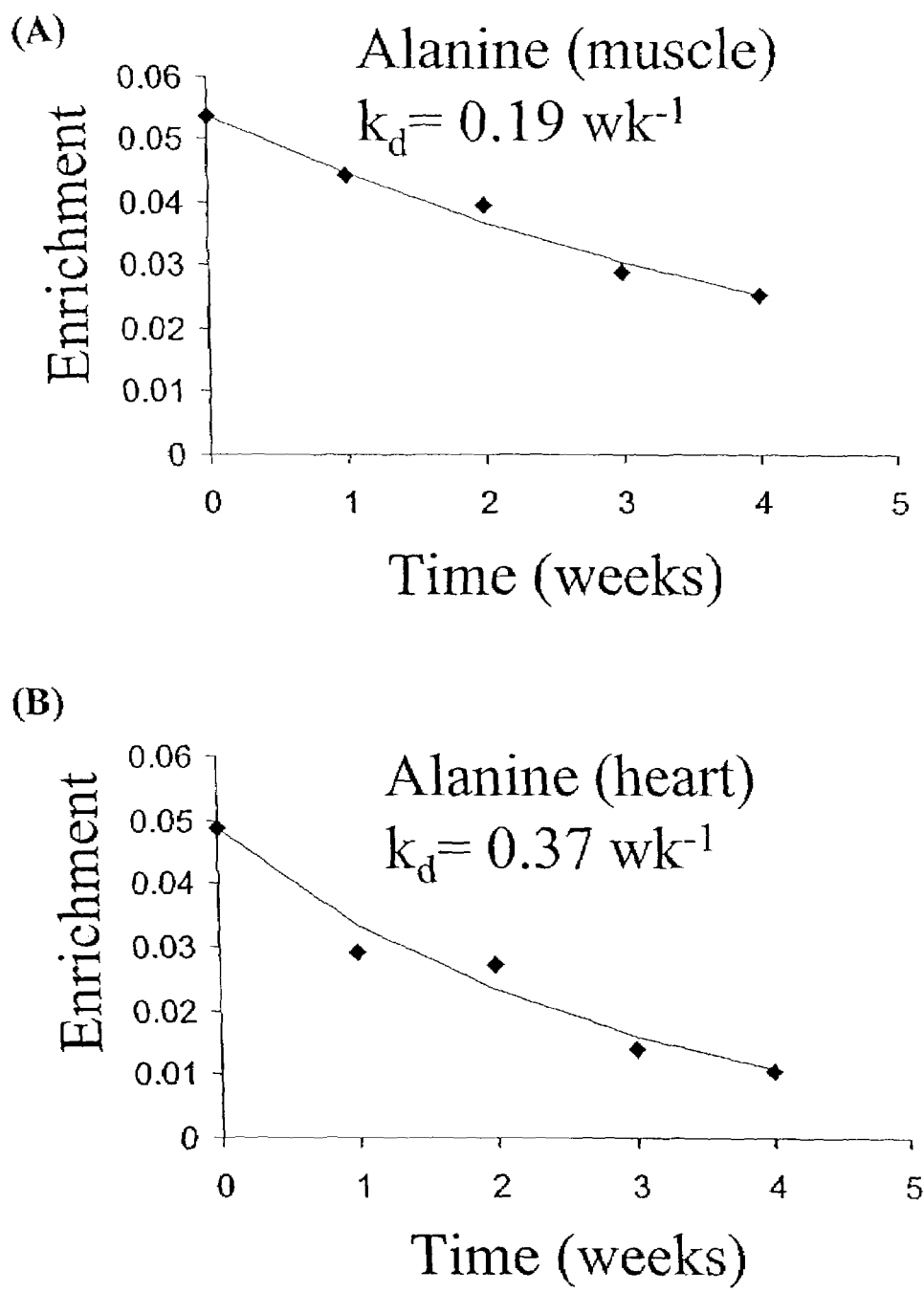
FIG. 15A depicts label decay curves for alanine isolated from skeletal muscle of rats, after discontinuing $^2H_2O$ intake in drinking water.
FIG. 15B depicts label decay curves for alanine isolated from heart muscle of rats, after discontinuing $^2H_2O$ intake in drinking water. Time zero is two weeks after discontinuing intake of $^2H_2O$, as shown in FIG. 11.

FIG. 11 depicts a washout of $^2H_2O$ from body $^2H_2O$ in rats and mice after discontinuing $^2H_2O$ administration in drinking water. Kinetic information can also be inferred from the label decay curves after cessation of $^2H_2O$ administration. Turnover of body water pools is relatively slow (FIG. 11), so that true label dilution did not begin until 10–14 days after discontinuing $^2H_2O$ administration (FIG. 15). Subsequent die-away curves (e.g. from weeks 3–6) reveal $k_d$. The rate constants calculated were similar to values obtained from label incorporation studies (e.g. $k_d$=0.19 wk$^{-1}$ for alanine in skeletal muscle proteins and $k_d$=0.37 wk$^{-1}$ for alanine in heart muscle proteins, FIG. 15).

Example 7

Discontinuous $^2H_2O$ Administration in Rats for Measuring Rat Muscle Rates

Figure 12:
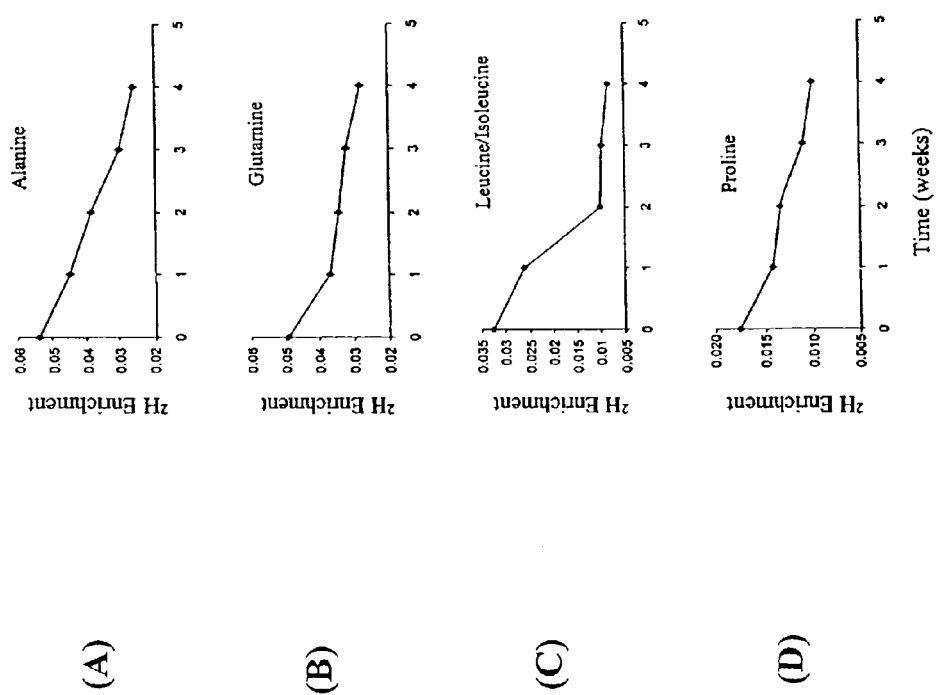
FIG. 12A depicts die-away curves of $^2H$-label in rat muscle protein-bound alanine (after discontinuing $^2H_2O$ administration).
FIG. 12B depicts die-away curves of $^2H$-label in rat muscle protein-bound glutamine (after discontinuing $^2H_2O$ administration).
FIG. 12C depicts die-away curves of $^2H$-label in rat muscle protein-bound leucine/isoleucine (after discontinuing $^2H_2O$ administration).
FIG. 12D depicts die-away curves of H-label in rat muscle protein-bound proline (after discontinuing $^2H_2O$ administration).

FIG. 12 depicts die-away curves of $^2H$-label in rat muscle protein-bound amino acids (after discontinuing $^2H_2O$ administration). Mixed proteins were isolated from hindlimb muscle (quadriceps femoris) and heart during 8–10 weeks of $^2H_2O$ administration (4% in drinking water) followed by a 6-week de-labeling period (re-institution of unlabeled drinking water). Rats were killed weekly (n=3/group) during the labeling and delabeling periods and skeletal muscle and heart were collected. Tissues were frozen in liquid $N_2$ at the time of sacrifice. Mixed proteins were hydrolyzed to free amino acids in 6N HCl, as described elsewhere (10). Amino acids were then derivatized for GC/MS analysis.

Example 8

Measurement of $^2H_2O$ Enrichment of Body Water by GC/MS

The $^2H_2O$ enrichment of body water was measured by a GC/MS technique that we have described elsewhere (Neese et al., Analytic Biochem 298(2):189–95, 2001). Briefly, the hydrogen atoms from water (10 μL) were chemically transferred to acetylene by reaction with calcium carbide in a sealed vial. Acetylene gas was then derivatized by injection into another sealed vial containing 0.5 ml $Br_2$ (0.1 mM) dissolved in $CCl_4$, followed by quenching of remaining $Br_2$ with cyclohexene. The resulting tetrabromoethane was dissolved in $CCl_4$ and was analyzed by GC/MS, using a DB-225 column (30 m, J&W, Folsom, Calif.) at 180° C., with methane chemical ionization (C.I.). The ions at m/z 265 and 266 were analyzed using selected ion monitoring. These ions represent the $M_0$ and $M_1$ mass isotopomers of the $C_2H_2Br_3^+$ fragment ($^{79}Br^{79}Br^{81}Br$ isotopologue). The enrichments of $^2H_2O$ in water samples were calculated by comparison to standard curves generated by mixing 100% $^2H_2O$ with unlabeled $H_2O$ in known proportions (Neese et al., Analytic Biochem 298(2):189–95, 2001).

Example 9

Measurement of Isotope Abundances of AA's by GC/MS

The mass isotopomer abundances of AA were analyzed as the N-acetyl, n-butyl ester derivative. Retention times of individual AA were established by use of unlabeled standards. The $M_0$–$M_2$ ions were analyzed for each NEAA, by selected ion monitoring (Table 1). The column was a DB225 at 120–220° C., with methane C.I. Adjustment of injection volumes was performed to maintain abundances of each NEAA within a range that allowed accurate measurement of isotope abundances.

Example 10

Number of Exchanging C—H Positions in AA and Determination of $A_1^\infty$

Two independent approaches were used for determining $A_x^\infty$ (the maximal isotopic enrichment of a particular mass isotopomer in a protein-bound AA during a continuous labeling protocol): combinatorial analysis (MIDA) and labeling to 100% replacement.

The ratio of excess double-labeled ($EM_2$):excess single-labeled ($EM_1$) AA molecules reflects the isotopic enrichment of-exchanging H-atoms (p) and the number of H-atoms actively exchanging (n), in accordance with principles of combinatorial probabilities. The ratio of $EM_2/EM_1$ in various non-essential AA was therefore measured as a means of calculating n (Table 1 and FIG. 2).

Table 3 shows the results of these experiments.

TABLE 3

Calculated values of n in free amino acids isolated from bone collagen in rats after $^2H_2O$ intake.

| Body water $^2H_2O$ | Alanine | | Glutamine | |
|---|---|---|---|---|
| | $EM_2/EM_1$ Ratio | Calculated n | $EM_2/EM_1$ Ratio | Calculated n |
| 0.0300 | 0.1493 | 3.45 | 0.2261 | 4.75 |
| 0.0290 | 0.1514 | 3.67 | 0.2287 | 5.03 |
| 0.0300 | 0.1514 | 3.57 | 0.2275 | 4.82 |
| 0.0310 | 0.1534 | 3.60 | 0.2352 | 5.10 |
| 0.0270 | 0.1531 | 3.97 | 0.2380 | 5.90 |
| 0.0310 | 0.1551 | 3.69 | 0.2314 | 4.90 |
| 0.0280 | 0.1504 | 3.70 | 0.2278 | 5.13 |
| 0.0310 | 0.1563 | 3.76 | 0.2293 | 4.79 |
| 0.0280 | 0.1498 | 3.66 | 0.2261 | 5.03 |
| 0.0280 | 0.1549 | 3.98 | 0.2372 | 5.67 |
| 0.0270 | 0.1508 | 3.83 | 0.2234 | 5.02 |
| 0.0290 | 0.1543 | 3.83 | 0.2252 | 4.83 |
| 0.0290 | 0.1518 | 3.69 | 0.2235 | 4.74 |
| 0.0290 | 0.1532 | 3.77 | 0.2184 | 4.45 |
| Mean ± S.D. | | 3.73 ± 0.15 | | 5.01 ± 0.37 |

Rats were given 4% $^2H_2O$ as drinking water for 5–11 weeks. Bone collagen was isolated and hydrolyzed to free AA as described in text and $EM_2/EM_1$ ratios were measured in hydrolysate alanine an glutamine. The measured body water enrichment in each animal was used to calculate a table of n as a function of theoretical $EM_2/EM_1$ ratios, using integral values of n (i.e., n = I, 2, 3, 4, 5), for each AA. The measured $EM_2/EM_1$ ratio in each AA was then plotted on the best-fit regression line calculated from the integral values of n, to calculate the best-fit value of n in the animal.

The MIDA-calculated values of actively exchanging H-positions were similar for bone collagen, muscle protein and in utero-labeled mixed proteins and revealed near-complete exchange for certain NEAA (e.g. calculated n for alanine≅4, for glycine≅2) under all the experimental conditions studied.

Isotope enrichments were measured in protein-bound alanine and glycine in different tissues isolated from rat pups labeled with $^2H_2O$ in utero (Table 4).

TABLE 4

Measured enrichments and calculated value of p and n for protein-bound glycine and alanine from different tissues in rat pups exposed to $^2H_2O$ in utero.

| Animal | Tissue | $EM_1$ | $EM_2$ | $EM_2/EM_1$ Ratio | Calc. P (n) |
|---|---|---|---|---|---|
| | | Protein-Bound Glycine | | | |
| 1 | Liver | 0.0403 | 0.0044 | 0.1088 | 2.60% (2) |
| | Muscle | 0.0396 | 0.0042 | 0.1071 | 2.30% (2) |
| | Brain | 0.0410 | 0.0044 | 0.1071 | 2.30% (2) |
| 2 | Liver | 0.0403 | 0.0044 | 0.1088 | 2.60% (2) |
| | Muscle | 0.0388 | 0.0042 | 0.1082 | 2.55% (2) |
| | Brain | 0.0412 | 0.0045 | 0.1104 | 2.83% (2) |
| 3 | Liver | 0.0425 | 0.0046 | 0.1074 | 2.38% (2) |
| | Brain | 0.0427 | 0.0047 | 0.1071 | 2.25% (2) |
| Mean ± SD | | 0.0408 ± 0.0013 | 0.0044 ± 0.0002 | 0.1086 | 2.48 ± 0.20% (2) |
| | | Protein-Bound Alanine | | | |
| 1 | Liver | 0.0821 | 0.0124 | 0.1510 | 2.57% (4) |
| | Muscle | 0.0824 | 0.0126 | 0.1529 | 2.67% (4) |
| | Brain | 0.0711 | 0.0103 | 0.1449 | 2.22% (4) |
| 2 | Liver | 0.0827 | 0.0126 | 0.1524 | 2.64% (4) |
| | Brain | 0.0691 | 0.0099 | 0.1433 | 2.33% (4) |
| Mean ± SD | | 0.0783 ± 0.0068 | 0.0116 ± 0.0013 | 0.1489 ± 0.0045 | 2.49 ± 0.20 (4) |

A female rat was started on 4% $^2H_2O$ in drinking water just prior to mating. The dam was maintained on 4% $^2H_2O$ throughout pregnancy and delivery. Within 24 hr of delivery, the mother and 3 pups were sacrificed. Blood was collected from the mother for measurement of body $^2H_2O$ enrichment. The pups were dissected and samples of liver, muscle and brain tissue were collected. Mixed proteins from these tissues were precipitated and hydrolyzed to free amino acids, as described in the text. Isotope enrichments in protein-bound glycine and alanine are shown, with calculated values of p ($^2H$-enrichment of exchanging H-atoms in the C—H backbone), assuming maximal values of n (i.e. full exchange). Alternatively, the mother's $^2H_2O$ enrichment was used to calculate n based on the measured $EM_2/EM_1$) ratio; the nearest integral value calculated for each sample is shown in parentheses. The mother's body $^2H_2O$ enrichment was 2.4%.

The calculated values of p for H-atoms entering each NEAA were very close to the measured body $^2H_2O$ enrichment in the mother at the time of sacrifice (2.49±0.20% calculated from alanine and 2.48±0.20% from glycine, compared to 2.4% from the measured $^2H_2O$ enrichment in maternal blood), when n=4 was used for the value of exchanging H-atoms in alanine and n=2 was used in glycine (i.e. complete exchange). Based on these calculated values of p and n, average protein fractional synthesis in these in utero-labeled animals was as expected, about 100% (99.8% for protein-bound glycine, 106% for protein-bound alanine).

These results support the validity of the combinatorial calculations and the underlying model for calculating p and n.

Example 11

Time Course of $^2$H-AA Labeling in Bone Collagen and Mixed Muscle Proteins

The time course of $^2$H incorporation from $^2H_2O$ into amino acids from bone collagen was measured in growing, adult mice (FIG. 13). The rate constant for rise to plateau ($k_s$) was similar for the NEAA tested (e.g. $k_{s(ala)}$=0.178 wk$^{-1}$, $k_{s(glyc)}$=0.163 wk$^{-1}$).

Administration of estrogen pellets (200 μg) to ovariectomized female rats resulted in a ca. 35–40% decrease in $k_s$ of bone collagen, compared to vehicle-implanted, ovariectomized rats (FIG. 14) from 0.012 to 0.008 d$^{-1}$. $^2$H incorporation into mixed proteins isolated from skeletal muscle was consistent for different AA. Values of $k_s$ for skeletal muscle were 0.21 wk$^{-1}$ (alanine) and 0.23 wk$^{-1}$ (glutamine). Replacement rates of mixed proteins from heart were higher (e.g. $k_s$=0.31 wk$^{-1}$, for alanine, in heart muscle proteins).

Example 12

In vitro Studies with $^2H_2O$

After incubation of an unlabeled protein (human serum albumin) in 70% $^2H_2O$ for 24 hr at room temperature and subsequent hydrolysis to free AA, no $^2$H incorporation was observed in any of the derivatized AA. Moreover, when $^2H_1$-labeled alanine (C—H bond labeled in carbon-2) or $^2H_2$-labeled glycine (C—H bond labeled in carbon-2) were subjected to the acid-hydrolysis conditions used for proteins, no loss of $^2$H-label was observed.

It is understood that the examples and embodiments described herein are for illustrative purposes only and that various modifications or changes in light thereof will be suggested to persons skilled in the art and are to be included within the spirit and purview of this application. All publications, patents and patent applications cited herein are hereby incorporated by reference in their entirety for all purposes to the same extent as if each individual publication, patent or patent application were specifically and individually indicated to be so incorporated by reference.

What is claimed is:

1. A method of determining the biosynthetic rate of one or more proteins or peptides in an individual comprising the steps of:
   (a) administering labeled water to an individual over a period of time sufficient for the label of said labeled water to be incorporated into said one or more proteins or peptides to form labeled and unlabeled proteins or peptides wherein said label is $^2$H, or $^{18}$O;
   (b) obtaining one or more bodily tissues or fluids from said individual, wherein said bodily tissues or fluids comprise said one or more labeled and unlabeled proteins or peptides; and
   (c) detecting the incorporation of said label in said one or more labeled proteins or peptides to determine the biosynthetic rate of said one or more proteins or peptides.

2. The method of claim 1 wherein said label is $^2$H.

3. The method according to claim 1 comprising the additional step of partially purifying said one or more labeled and unlabeled proteins or peptides from said bodily tissues or fluids before step (c).

4. The method according to claim 1 wherein step (c) includes detection of said one or more labeled or unlabeled proteins or peptides by mass spectrometry.

5. The method according to claim 1 wherein said labeled water is administered orally.

6. The method according to claim 1 wherein:
   following step (b), the method includes the additional step of hydrolyzing said one or more proteins or peptides to produce hydrolyzed amino acids, and optionally, oligopeptides.

7. The method according to claim 6, wherein:
   step (c) includes detecting incorporation of said label into said amino acids or oligopeptides.

8. The method according to claim 6, wherein said hydrolyzed amino acids or oligopeptides are separated by gas chromatography or HPLC.

9. The method according to claim 1 wherein said individual is a human.

10. A method of determining the biosynthetic rate of one or more proteins or peptides in an individual comprising the steps of:
    (a) administering labeled water to an individual over a period of time sufficient for the label of said labeled water to be incorporated into said one or more proteins or peptides and thereby form labeled and unlabeled proteins or peptides wherein said label is $^2$H or $^{18}$O;
    (b) obtaining one or more bodily tissues or fluids from said individual, wherein said bodily tissues or fluids comprise said one or more labeled and unlabeled proteins or peptides;
    (c) hydrolyzing said one or more labeled and unlabeled proteins to produce one or more labeled and unlabeled amino acids or oligopeptides;
    (d) detecting the incorporation of said label in said one or more labeled amino acids or oligopeptides to determine the biosynthetic rate of said one or more proteins or peptides.

11. The method of claim 10 wherein said label $^2$H.

12. The method according to claim 10, wherein the one or more labeled and unlabeled amino acids or oligopeptides are separated by gas chromatography or HPLC.

13. The method according to claim 10 wherein said one or more proteins or peptides are selected from the group consisting of full length proteins or peptide fragments of bone collagen, liver collagen, lung collagen, cardiac collagen, muscle myosin, serum hormone, plasma apolipoproteins, serum albumin, clotting factor, immunoglobulin, and mitochondrial protein.

14. The method of claim 10 wherein said individual is a human.

* * * * *

UNITED STATES PATENT AND TRADEMARK OFFICE
CERTIFICATE OF CORRECTION

PATENT NO. : 7,001,587 B2  
APPLICATION NO. : 10/279399  
DATED : February 21, 2006  
INVENTOR(S) : Marc K. Hellerstein Page 1 of 1

It is certified that error appears in the above-identified patent and that said Letters Patent is hereby corrected as shown below:

At Column 30, Line 52, Claim 1,

Currently reads: "The method of claim 10 wherein said label $^2$H."

Should read: -- The method of claim 10 wherein said label is $^2$H --.

Signed and Sealed this

Twenty-fifth Day of December, 2007

JON W. DUDAS  
*Director of the United States Patent and Trademark Office*